United States Patent [19]

Sohda et al.

[11] Patent Number: 5,496,834
[45] Date of Patent: Mar. 5, 1996

[54] LACTOL DERIVATIVES, THEIR PRODUCTION AND USE

[75] Inventors: Takashi Sohda, Osaka; Yukio Fujisawa, Hyogo; Satoru Oi, Nara; Junji Mizoguchi, Osaka, all of Japan

[73] Assignee: Takeda Chemical Industries, Ltd., Osaka, Japan

[21] Appl. No.: 300,738

[22] Filed: Sep. 2, 1994

[30] Foreign Application Priority Data

| Sep. 3, 1993 | [JP] | Japan | 5-219655 |
| Jul. 20, 1994 | [JP] | Japan | 6-168501 |
| Aug. 12, 1994 | [JP] | Japan | 6-190385 |

[51] Int. Cl.$^6$ .......................... A61K 31/44; A61K 31/40; A61K 31/35
[52] U.S. Cl. .......................... 514/343; 514/411; 514/419; 514/459; 514/461; 546/164; 546/283; 546/268; 546/275; 548/440; 548/441; 548/444; 548/467; 549/419; 549/475
[58] Field of Search .......................... 549/419, 475; 514/459, 461, 343, 411, 419; 546/164, 283, 268, 275; 548/440, 441, 444, 467

[56] References Cited

FOREIGN PATENT DOCUMENTS

| 0504938 | 12/1992 | European Pat. Off. |
| 0519748 | 12/1992 | European Pat. Off. |

OTHER PUBLICATIONS

Alves, R. J., et al., J. Carbohydrate Chemistry 10(6):1049–1057 (1991).
Can. J. of Chemistry, 60, 558 (1982).
Can. J. of Chemistry, 56, 119 (1978).
Tet. Lett., 30, 5421 (1989).
Chem. Pharm. Bull., 16, 1881 (1968).
Eur. J. Med. Chem. 12, 317 (1977).
Biochem. Biophys. Res. Comm., 49, 343 (1972).
JO 2304–085–A (May 18, 1989).

*Primary Examiner*—C. Warren Ivy
*Assistant Examiner*—Amelia Owens
*Attorney, Agent, or Firm*—David G. Conlin; Ronald I. Eisenstein

[57] ABSTRACT

The present invention provides novel compound of the formulas (Ia) or (I):

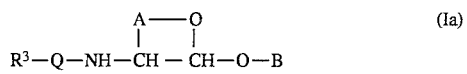

wherein Q is one or two amino acid residues which may be substituted; $R^3$ is a carboxyl group which may be esterified or an acyl group; A is an alkylene group; B is hydrogen or an alkyl group which may be substituted or an acyl group; or a salt thereof;

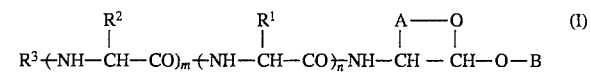

wherein $R^1$ and $R^2$ may be the same or different and each is hydrogen or a hydrocarbon residue which may be substituted; $R^3$, A and B have the same definitions as those shown above; m and n each is 0 or 1; provided that where both m and n are both equal to 0, $R^3$ is a carboxyl group which may be esterified or an acyl group having not less than 7 carbon atoms; or a salt thereof.

The compound (Ia) or (I) shows cathepsin L inhibitory and bone resorption inhibitory activities and are useful as a prophylactic/therapeutic agent for osteoporosis.

22 Claims, No Drawings

LACTOL DERIVATIVES, THEIR PRODUCTION AND USE

FIELD OF THE INVENTION

This invention relates to a lactol derivative having cathepsin L inhibitory and bone resorption inhibitory activities or a salt thereof, their production and a pharmaceutical composition for the prophylaxis or therapy of osteoporosis which comprises said derivative or a pharmaceutically acceptable salt thereof as an active ingredient.

BACKGROUND OF THE INVENTION

Osteoporosis is a pathologic state or disease entity characterized by a loss of bone mass over a certain level thereby giving rise to certain symptoms or increasing one's risk for getting the symptoms. Its major symptoms are spinal kyphosis and compression fracture of the dorsolumbar vertebrae and vertebral bodies, neck of the femur, distal end of the radius, the rib, proximal end of the humerus, and other bones. In bone tissues, normally bone formation and resorption are going on at matched rates, with osteoblasts and osteoclasts playing central roles in the formation and resorption, respectively. However, when the balance of bone formation and bone resorption is disrupted in favor of resorption, a net loss of bone mass results. Therefore, drugs capable of inhibiting bone resorption are considered useful for the prophylaxis and therapy of osteoporosis and several bone resorption inhibitors such as estrogens and calcitonins have been suggested in the treatment of osteoporosis. However, these drugs have various deficiencies, some are restricted in the scope of indication and/or indefinite in efficacy so that no satisfactory responses have been clinically obtained others can be associated with various other health risks. Therefore, a demand exists for a new prophylactic/therapeutic regimen for increased bone resorption.

Recently it has become clear that cathepsin L, a protease secreted from osteoclasts in the process of resorption, is a major factor in the degradation of the bone matrix protein, collagen. Therefore, it is believed that the decomposition of bone collagen due to resorption can be controlled by inhibiting cathepsin L activity and that this approach is useful for the prophylaxis and therapy of osteoporosis. Heretofore, a few substances including leupeptin and antipain as well as the epoxysuccinic acid derivatives disclosed in Japanese published unexamined patent application (Kokai tokkyo koho hei) Nos.2-304074, 2-304075 and 2-304085 are reported to have cathepsin L inhibitory activity as one of their inhibition activities.

Lactol derivatives having an 3-amino-2-hydroxyfuran or 3-amino-2-hydroxypyran skeleton namely, the compounds described in Tetrahedron Letters, 30, 5421 (1989), Canadian Journal of Chemistry, 60, 558 (1982), Canadian Journal of Chemistry, 56, 119 (1978), European Journal of Medicinal Chemistry, 12, 317 (1977), and Chemical and Pharmaceutical Bulletin, 16, 1881 (1968) [all of which are incorporated herein by reference], for instance, are known. However, none of the literature allude to these compounds having any cathepsin L inhibitory activity. Nor is any compound formed by coupling the 3-amino group of the 3-amino-2-hydroxyfuran or 3-amino-2-hydroxypyran skeleton to an amino acid derivative known.

However, epoxysuccinic acid derivatives inhibit not only cathepsin L but also other proteases as acknowledged in the above patent literature, but those compounds have not been implemented as a prophylactic/therapeutic drug for osteoporosis.

SUMMARY OF THE INVENTION

The inventors of this invention did much research to develop an easy-to-use drug which would show specific cathepsin L inhibitory activity and act directly on the bone to inhibit bone resorption. As a consequence, they discovered that a lactol derivative of the following general formula (Ia) or (Ib) has potent cathepsin L inhibitory activity and acts directly on the bone displaying an outstanding bone resorption inhibitory action. This invention has been developed on the basis of the above findings.

Accordingly, the present invention relates to:

(1) A compound of the formula (Ia)

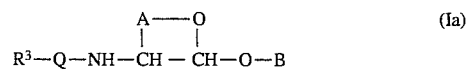

wherein Q represents one or two amino acid residues which may or may not be substituted; $R^3$ represents a carboxyl group which may or may not be esterified or an acyl group; A represents an alkylene group; B represents hydrogen, an alkyl group which may or may not be substituted or an acyl group, or a salt of the compound, (2) A compound of the formula (I)

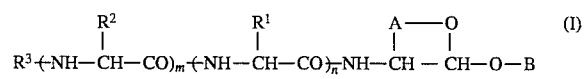

wherein $R^1$ and $R^2$ may be the same or different and each represents hydrogen or a hydrocarbon group which may or may not be substituted; $R^3$ represents a carboxyl group which may or may not be esterified or an acyl group; A represents an alkylene group; B represents hydrogen, an alkyl group which may be substituted or an acyl group; m and n each represents 0 or 1 and may be the same or different; provided that where both m and n are equal to 0, $R^3$ represents a carboxyl group which may be esterified or an acyl group having not less than 7 carbon atoms, or a salt of the compound, (3) The compound of the above item (1) or (2) wherein A represents a $C_{2-4}$ lower alkylene group, or a salt of the compound, (4) The compound of the above item (1) or (2) wherein the alkyl group for B which may or may not be substituted represents a $C_{1-4}$ lower alkyl group which may or may not be substituted, or a salt of the compound, (5) The compound of the above item (1) or (2) wherein the acyl group for B represents an acyl group derived from a carboxylic acid which may or may not be substituted or a salt of the compound, (6) The compound of the above item (2) wherein the hydrocarbon group for $R^1$ or $R^2$, which may be substituted, represents an aryl group which may or may not be substituted or an aliphatic hydrocarbon group which may or may not be substituted, or a salt of the compound, (7) The compound of the above item (6) wherein the aryl group for $R^1$ or $R^2$ which may or may not be substituted represents a $C_{6-14}$ aromatic hydrocarbon group of a monocyclic or a condensed polycyclic system, or a 5- or 6-membered heteroaromatic group, or a salt of the compound, (8) The compound of the above item (6) wherein the aliphatic hydrocarbon group for $R^1$ or $R^2$ which may or may not be substituted represents (i) a saturated $C_{1-8}$ aliphatic hydrocarbon group, (ii) an unsaturated $C_{2-8}$ aliphatic hydrocarbon group, (iii) a saturated $C_{3-7}$ alicyclic hydrocarbon group, (iv) an unsaturated $C_{5-7}$ alicyclic hydrocarbon group or (v) a saturated $C_{1-8}$ aliphatic hydrocarbon group which is substituted by a alicyclic hydrocarbon group, or a salt of the compound, (9) The compound of the above item (2) wherein $R^1$ or $R^2$ represents a lower alkyl group, or a salt of the compound,

(10) The compound of the above item (2) wherein $R^1$ or $R^2$ represents a arylalkyl group, or a salt of the compound,

(11) The compound of the above item (1) or (2) wherein the acyl group for $R^3$ represents an acyl group derived from the group consisting of a carboxylic acid, a sulfonic acid, a sulfinic acid, a carbamic acid and a thiocarbamic acid, all of which may or may not be substituted, or a salt of the compound,

(12) The compound of the above item (2) wherein m represents 1 and n represents 1, or a salt of the compound,

(13) The compound of the above item (2) wherein m represents 1 and n represents 0, or a salt of the compound,

(14) The compound of the above item (2) wherein m represents 0 and n represents 0, or a salt of the compound,

(15) A process for producing a compound of the formula (Ia)

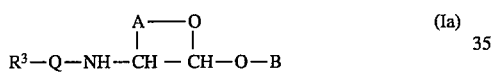

wherein Q represents one or two amino acid residues which may or may not be substituted; $R^3$ represents a carboxyl group which may or may not be esterified or an acyl group; A represents an alkylene group; B represents hydrogen or an alkyl group which may or may not be substituted or an acyl group; wherein the process comprises subjecting a compound of the formula (IIa)

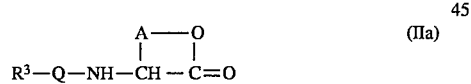

wherein $R^3$, Q and A are as defined above to a reduction reaction,

(16) The process of the above item (15), which further comprises subjecting the compound formed to an alkylation or acylation reaction.

(17) A process for producing a compound of the formula (I)

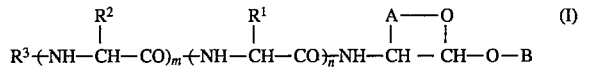

wherein $R^1$ and $R^2$ may be the same or different and each represents hydrogen or a hydrocarbon residue which may or may not be substituted; $R^3$ represents a carboxyl group which may or may not be esterified or an acyl group; A represents an alkylene group; B represents hydrogen, an alkyl group which may or may not be substituted or an acyl group; m and n each represents 0 or 1; provided that where both m and n are equal to 0, $R^3$ represents a carboxyl group which may or may not be esterified or an acyl group having not less than 7 carbon atoms, or a salt thereof; wherein the process comprises subjecting a compound of the general formula (II)

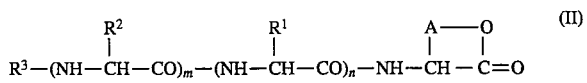

wherein $R^1$, $R^2$, $R^3$ and A are as defined above, to a reduction reaction,

(18) The process of the above item (17), which further comprises subjecting the compound formed to an alkylation or acylation reaction.

(19) A cathepsin L inhibitory composition comprising a compound of the formula (Ia) or a pharmaceutically acceptable salt of the compound,

(20) A cathepsin L inhibitory composition comprising a compound of the formula (Ib)

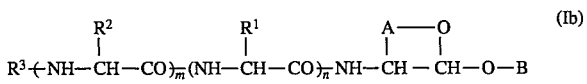

wherein $R^1$ and $R^2$ may be the same or different and each represents hydrogen or a hydrocarbon group which may or may not be substituted; $R^3$ represents a carboxyl group which may or may not be esterified or an acyl group; A represents an alkylene group; B represents hydrogen, an alkyl group which may or may not be substituted or an acyl group; m and n each represents 0 or 1, or a pharmaceutically acceptable salt of the compound,

(21) A bone resorption inhibitory composition comprising a compound of the formula (Ia) or a pharmaceutically acceptable salt of the compound,

(22) A bone resorption inhibitory composition comprising a compound of the formula (Ib), or a pharmaceutically acceptable salt of the compound,

(23) A bone resorption inhibitory composition of the above item (21) or (22) for the prophylaxis or therapy of osteoporosis.

DESCRIPTION OF THE PREFERRED EMBODIMENTS

The various terms and definitions used in this specification are now explained in detail below.

The constituent amino acids relevant to this invention are L-configured unless otherwise indicated and the corresponding abbreviations such as Gly for glycine, Leu for leucine and Ile for isoleucine conform to the nomenclature recommended by International Union of Pure and Applied Chemistry (IUPAC)-International Union of Biochemistry (IUB). The skilled artisan can readily select amino-protecting groups that can be used in this invention as protective groups for amino groups are well known in this field of art. Preferred protecting groups are acetyl, benzyloxycarbonyl, 4-methoxybenzyloxycarbonyl, t-butoxycarbonyl, phthalyl and formyl, among others. Particularly preferred is benzyloxycarbonyl.

The lactol derivatives of this invention are compounds that are structurally quite different from the formerly known substances having cathepsin L inhibitory activities. No lactol derivatives having cathepsin L inhibitory activities, among those having the structure 3-amino-2-hydroxyfuran or 3-amino-2-hydroxypyran, are known. And the lactol derivatives of this invention are compounds which have a new structure as a result of coupling the 3-amino group of them to an amino acid derivative.

In the above formulas, the amino acid residue represented by Q which may be substituted includes any natural or non-natural, L-type or D-type α-amino acids. Said amino acid residue may for example be α-L-amino acid or α-D-amino acid which is the constituent of natural proteins (e.g. glycine, α-L- or α-D-, alanine, valine, leucine, isoleucine, serine, threonine, asparagine, glutamine, aspartic acid, glutamic acid, lysine, arginine, cysteine, methionine, phenylalanine, tyrosine, tryptophan, histidine, proline, etc.-), glycine, α-L-, alanine, valine, leucine, isoleucine, phenylalanine, tyrosine, methionine and aspartic acid are preferred.

In the above formulas, the amino acid residue represented by Q which may be substituted may have 1 to 3 suitable substituents at chemically synthesizable position. The substituents are the same meaning as those exemplified hereinafter as substituents of an aromatic hydrocarbon group, a heteroaromatic group and an aliphatic hydrocarbon group represented by $R^1$ and $R^2$, each of which may be substituted.

Referring to the general formulas presented above, the hydrocarbon residue which may be substituted or unsubstituted, $R^1$ and $R^2$, may for example be an aryl group or an aliphatic hydrocarbon group.

The aryl group which may be substituted, as an example of the hydrocarbon group which may be substituted, $R^1$ and $R^2$, include a $C_{6-14}$ aromatic hydrocarbon group of the monocyclic or condensed polycyclic system, and a 5- or 6-membered heteroaromatic-group-containing 1–2 nitrogen atoms and one sulfur or oxygen atom etc. The heteroaromatic group mentioned above may each be fused to a 6-membered ring containing not more than 2 nitrogen atoms, a benzene ring or a 5-membered ring containing one sulfur atom.

Among such aromatic hydrocarbon group mentioned above, they preferably include phenyl, naphthyl, anthryl, phenanthryl, acenaphthylenyl and so on.

Among such heteroaromatic group mentioned above, they preferably include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol- 3-yl, 1,2,3-triazol-4-yl, tetrazol-5-yl, benzimidazol-2-yl, indol-3-yl, 1H-indazolyl, benzo[b]furanyl, isobenzofuranyl, benzo[b]thienyl, 1H-pyrrolo[2,3-b]pyrazin-2-yl, 1H-pyrrolo[2,3-b]pyridin-2-yl, 1H-imidazo[4,5-b]pyridin-2-yl, 1H-imidazo[4,5-c]pyridin-2-yl, 1H-imidazo[4,5-b]pyrazin-2-yl and so on.

The aliphatic hydrocarbon group which may be substituted, as an example of $R^1$ or $R^2$, includes:

(i) saturated aliphatic hydrocarbon group of 1–8 carbon atoms ($C_{1-8}$ alkyl groups) such as methyl, ethyl, propyl, isopropyl, butyl, isobutyl, sec-butyl, t-butyl pentyl, isopentyl, neopentyl, t-pentyl, hexyl, isohexyl, heptyl, octyl, etc., (ii) unsaturated aliphatic hydrocarbon group of 2–8 carbon atoms ($C_{2-8}$ alkenyl groups) such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, etc., or ($C_{2-8}$ alkynyl groups) such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl, etc., (iii) saturated alicyclic hydrocarbon group of 3–7 carbon atoms ($C_{3-7}$ cycloalkyl groups) such as cyclopropyl, cyclobutyl, cyclopentyl, cyclohexyl, cycloheptyl, etc., (iv) unsaturated alicyclic hydrocarbon group of 5–7 carbon atoms ($C_{5-7}$ cycloalkenyl groups) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc., (v) Saturated aliphatic hydrocarbon group of 1–8 carbon atoms which is substituted by saturated or unsaturated alicyclic hydrocarbon group mentioned above ($C_{3-7}$ cycloalkyl-$C_{1-8}$ alkyl groups or $C_{5-7}$ cycloalkenyl-$C_{1-8}$ alkyl groups, etc., such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, and so on.

The aromatic hydrocarbon group, heteroaromatic hydrocarbon group or aliphatic hydrocarbon group, each of which may be substituted, represented by $R^1$ and $R^2$ in the above formulas, may have 1–3 substituent groups in chemically synthesizable positions. As such substituent groups, there may be mentioned aryl group, aliphatic hydrocarbon group, non-aromatic heterocyclic group, acyl group, carboxyl which may be esterified, amino which may be substituted, hydroxyl which may be substituted, thiol which may be substituted, a halogen atom, a nitro group, or a phosphono group which may be substituted.

As said aryl group and aliphatic hydrocarbon group, the same group as the aryl and aliphatic hydrocarbon group as already mentioned for $R^1$ and $R^2$ are included.

The non-aromatic heterocyclic group includes a 5- through 7-membered heterocyclic group each containing one sulfur, nitrogen or oxygen atom, or a 5- or 6-membered heterocyclic group containing 2–4 nitrogen atoms, such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homopiperidyl, pyrrolinyl, imidazolidinyl and so on. These non-aromatic heterocyclic groups may each be fused to a benzene ring, a 6-membered ring containing not more than 2 nitrogen atoms or a 5-membered ring containing one sulfur atom. Such fused non-aromatic heterocyclic group includes chromanyl, isochromanyl, indolinyl, isoindolinyl, thiochromanyl, isothiochromanyl and so on.

The acyl group represents that derived from the group consisting of a carboxylic acid, a sulfonic acid, a sulfinic acid, a carbamic acid or a thiocarbamic acid and so on which may be substituted, such as the groups represented by the formulas, —$COR^4$, —$SO_2R^6$, —$SOR^{10}$, —$CONHR^7$, —$CSNHR^8$, wherein $R^4$, $R^6$, $R^7$, $R^8$ and $R^{10}$ may be the same or different and each represents a hydrocarbon group which may be substituted. Said hydrocarbon group which may be substituted as represented by $R^4$, $R^6$, $R^7$, $R^8$ or $R^{10}$ may be those mentioned for the hydrocarbon groups which may be substituted, $R^1$ and $R^2$.

The acyl group mentioned above preferably includes the group represents by the formula —$COR^9$ wherein $R^9$ represents hydrogen, a $C_{1-10}$ alkyl, a $C_{2-10}$ alkenyl or a aromatic group (e.g. formyl, acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexencarbonyl, benzoyl, nicotinoyl, etc.).

The carboxyl group which may be esterified includes the group, for example, represented by the formula —$COOR^5$, wherein $R^5$ represents a $C_{1-6}$ alkyl, a $C_{2-6}$ alkenyl or a $C_{6-10}$ aralkyl, such as those resulting from binding of a carboxyl group and an alkyl group having 1 to 6 carbon atoms, that is a $C_{1-6}$ alkoxycarbonyl (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.), binding of a carboxyl group and an alkenyl group having 2 to 6 carbon atoms, that is a $C_{2-6}$ alkenyloxycarbonyl (e.g. allyloxycarbonyl, crotyloxycarbonyl, 2-pentenyloxycarbonyl, 3-hexenyloxycarbonyl, etc.), or binding of a carboxyl group and an aralkyl group having 6 to 10 carbon atoms, that is a $C_{6-10}$ aralkyloxycarbonyl (e.g. benzyloxycarbonyl, phenethyloxycarbonyl, etc.).

The amino group mentioned above which may or may not be substituted includes amino or amino (—$NH_2$) as mono- or di-substituted by $C_{1-10}$ alkyl, $C_{2-10}$ alkenyl, aromatic groups or acyl group (e.g. methylamino, dimethylamino, ethylamino, diethylamino, dibutylamino, diallylamino, cyclohexylamino, phenylamino, N-methyl-N-phenylamino, acetylamino, benzoylamino, etc.).

The hydroxyl group mentioned above which may or may not be substituted includes hydroxyl or hydroxyl having a suitable substituent, particularly one that can be used as a hydroxyl-protecting group, for example alkoxy, alkenyloxy, aralkyloxy, acyloxy, even aryloxy and so on.

The alkoxy group mentioned above is preferably a $C_{1-10}$ alkoxy group (e.g. methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, cyclohexyloxy, etc.).

The alkenyloxy group mentioned above is preferably a $C_{2-10}$ alkenyloxy group (e.g. allyloxy, crotyloxy, 2-pentenyloxy, 3-hexenyloxy, 2-cyclopentenylmethoxy, 2-cyclohexenylmethoxy, etc).

The aralkyloxy group that can be used includes phenyl-$C_{1-4}$ alkyloxy (e.g. benzyloxy, phenethyloxy, etc.), among others.

The acyloxy group mentioned above is preferably a $C_{2-4}$ alkanoyloxy group (e.g. acetyloxy, propionyloxy, n-butyryloxy, isobutyryloxy, etc.).

The aryloxy group includes phenoxy and 4-chlorophenoxy, among others.

The thiol group which may or may not be substituted includes thiol and thiol having a suitable substituent, particularly one which can be used as a thiol-protecting group, for example alkylthio, aralkylthio and acylthio, among others.

The alkylthio mentioned above is preferably a $C_{1-10}$ alkylthio group (e.g. methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio, etc.).

The aralkylthio group mentioned above is preferably a phenyl-$C_{1-4}$ alkylthio (e.g. benzylthio, phenethylthio, etc.), among others.

The acylthio group is preferably a $C_{2-4}$ alkanoylthio group (e.g. acetylthio, propionylthio, n-butyrylthio, isobutyrylthio, etc.).

The halogen may for example be fluorine, chlorine, bromine or iodine and is preferably fluorine or chlorine.

The phosphono group which may by substituted may for example be dimethoxyphosphoryl, diethoxyphosphoryl, dipropoxyphosphoryl, diisopropoxyphosphoryl, ethylenedioxyphosphoryl, trimetylenedioxyphosphoryl, tetrametylenedioxyphosphoryl, and so on.

Preferred examples of $R^1$ and $R^2$ are respectively hydrogen, a lower alkyl group or a aryl(lower)alkyl group, particularly a straight-chain or branched $C_{1-5}$ alkyl or a phenyl $C_{1-5}$ alkyl group, which may be substituted by optionally substituted hydroxyl or thiol as mentioned above, which include $CH_3$—S—$CH_2$—$CH_2$—,

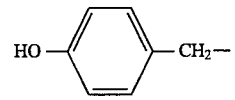

In the above formulas, $R^3$ represents a carboxyl group which may be esterified or an acyl group. Provided that where both m and n are equal to 0 with respect to formula (I) or (II), $R^3$ represents a carboxyl group which may be esterified or a acyl group having not less than 7 carbon atoms, particularly a carboxyl group which may be esterified or a acyl group having 7–50 carbon atoms.

The carboxyl group which may be esterified, as represented by $R^3$ in the above formulas, has the same meaning as those exemplified hereinbefore as the substituent group of an aromatic hydrocarbon group, a heteroaromatic hydrocarbon group and an aliphatic hydrocarbon group represented by $R^1$ and $R^2$, and preferred example of $R^3$ is an alkoxycarbonyl group (e.g. methoxycarbonyl, ethoxycarbonyl, tert-butoxycarbonyl, phenoxycarbonyl, benzyloxycarbonyl, etc.), particularly benzyloxycarbonyl.

The acyl group represented by $R^3$ has the same meaning as those exemplified hereinbefore as the substituent group of an aromatic hydrocarbon group, a heteroaromatic hydrocarbon group and an aliphatic hydrocarbon group represented by $R^1$ and $R^2$.

These alkoxycarbonyl groups which may be substituted or acyl groups represented by $R^3$ may have 1 to 3 suitable substituent group, which is the same acyl group, carboxyl group which may be esterified, amino group which may be substituted, hydroxyl group which may be substituted, thiol group which may be substituted, halogen atom, nitro group or phosphono group which may be substituted as mentioned above, in chemically synthesizable position.

In the above formulas, the alkylene group A represents an alkylene group of 2–4 in carbon number, particularly ethylene or propylene.

B in the above formulas is preferably hydrogen.

The alkyl group which may be substituted, as represented by B in the above formulas, includes a $C_{1-6}$ lower alkyl group which may be substituted (e.g. methyl, ethyl, propyl, isopropyl, butyl, isobutyl, sec-butyl, tert-butyl, pentyl, isopentyl, hexyl etc.).

The acyl group which may be substituted, represented by B in the above formulas, has the same meaning as those exemplified hereinbefore as the substituent group of an aromatic hydrocarbon group, a heteroaromatic hydrocarbon group and an aliphatic hydrocarbon group represented by $R^1$ and $R^2$.

These alkyl groups which may be substituted or the acyl groups which may be substituted represented by B may have 1 to 3 suitable substituent group, which is the same acyl group, carboxyl group which may be esterified, amino group which may be substituted, hydroxyl group which may be substituted, thiol group which may be substituted, halogen atom, nitro group or phosphono group which may be substituted as mentioned above, in chemically synthesizable position.

The salt of compound (Ia) or (Ib) of this invention is preferably a pharmaceutically acceptable salt, including salts with inorganic bases, salts with organic bases, salts with inorganic acids, salts with organic acids, and salts with basic or acidic amino acids. Salts are well known in the art as is their preparation.

The preferred inorganic salts are salts with alkali metals such as sodium, potassium, etc., salts with alkaline earth metals such as calcium, magnesium, etc., aluminum salt and ammonium salts, among others.

The preferred salts with organic bases are salts with trimethylamine, triethylamine, pyridine, picoline, ethanolamine, diethanolamine, triethanolamine, dicyclohexylamine, N,N'-dibenzylethylenediamine and so on.

The preferred salts with inorganic acids are salts with hydrochloric acid, hydrobromic acid, nitric acid, sulfuric acid, phosphoric acid and so on. The preferred salts with organic acids are salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and so on.

The preferred salts with basic amino acids are salts with arginine, lysine, ornithine and so on, while the preferred salts with acidic amino acids are salts with aspartic acid, glutamic acid and so on.

The synthetic procedures for the compound of this invention is now described in detail.
Process A

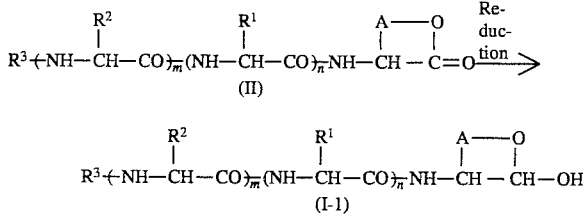

wherein all symbols have the meanings as defined hereinbefore.

In this process, compound (II) is reduced to compound (I-1). This reduction reaction can be carried out in a manner known in that art. For example, reduction with a metal hydride, reduction with a metal hydrogen complex compound, reduction with diborane or a substituted diborane, and catalytic hydrogenation can be utilized. Thus, this reaction can be carried out by treating compound (II) with a reducing agent.

The reducing agent includes alkali metal borohydrides (e.g. sodium borohydride, lithium borohydride, etc.), metal hydrogen complex compounds such as lithium aluminum hydride, metal hydrides such as sodium hydride, organotin compounds (e.g. triphenyltin hydride), metals and metal salts such as nickel compounds, zinc compounds, etc., a catalytic reduction system using a transition metal catalyst, e.g. palladium, platinum or rhodium, in combination with hydrogen, and diborane, among others. Particularly, the reaction can be carried out advantageously using diisobutylaluminum hydride.

This reaction is conducted in an organic solvent that does not interfere with the reaction. Such solvents are known in the art. The solvent, thus, includes aromatic hydrocarbons such as benzene, toluene, xylene, etc., halogenated hydrocarbons such as chloroform, carbon tetrachloride, dichloromethane, 1,2-dichloroethane, 1,1,2,2-tetrachloroethane, etc., ethers such as diethyl ether, tetrahydrofuran, dioxane, etc., alcohols such as methanol, ethanol, propanol, isopropyl alcohol, 2-methoxyethanol, etc., amides such as N,N-dimethylformamide etc., among others. These solvents can be selectively employed, alone or in combination, according to the type of reducing agent employed.

The reaction temperature is −100° C. −150° C., preferably −80° C. −100° C., and the reaction time is about 1–24 hours.

The lactol derivative (I-1) thus obtained can be separated and purified by known isolation-purification procedures such as concentration, concentration under reduced pressure, solvent extraction, crystallization, recrystallization, redistribution, chromatography and so on.

The starting compound (II) for use in this invention can be prepared by the following and other processes.
Process B

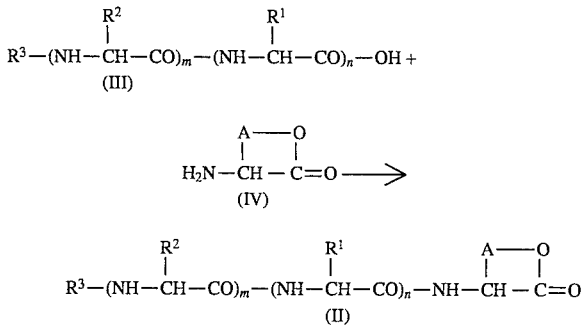

wherein all symbols have the meanings as defined hereinbefore.

In this process, compound (III) or a reactive derivative of the carboxyl group thereof, or a salt thereof, is reacted with compound (IV) or a reactive derivative of the amino group thereof, or a salt thereof, to provide compound (II).

The preferred reactive derivative of the amino group of compound (IV) includes a Schiff base type imino or enamine form tautomer, which is obtainable by reacting compound (IV) with a carbonyl compound such as an aldehyde or a ketone, a silyl derivative obtainable by reacting compound (IV) with a silyl compound such as bis(trimethylsilyl)acetamide, mono(trimethylsilyl)acetamide, bis(trimethylsilyl)urea or the like, and a derivative obtainable by reacting compound (IV) with phosphorus trichloride or phosgene.

For the preferred salts of compound (IV) or its reactive derivative, the acid addition salts mentioned for compound (I) are incorporated here by reference.

The preferred reactive derivative of the carboxyl group of compound (III) includes acid halides, acid anhydrides, activated amides, activated esters and so on. The preferred examples of such reactive derivative include acid chlorides; acid azides; mixed acid anhydrides with various acids such as substituted phosphoric acids, e.g. dialkylphosphoric acid, phenylphosphoric acid, diphenyl-phosphoric acid, dibenzylphosphoric acid, halophosphoric acids, etc., dialkylphosphorous acids, sulfurous acid, thiosulfuric acid, sulfuric acid, sulfonic acids such as methanesulfonic acid etc., aliphatic carboxylic acids such as acetic acid, propionic acid, lactic acid, isolactic acid, pivalic acid, pentanoic acid, isopentanoic acid, trichloroacetic acid, etc., aromatic caroboxylic acids Such as benzoic acid etc.; symmetric acid anhydride; activated amides with imidazole, 4-substituted imidazoles, dimethylpyrazole, triazole, tetrazole, etc.; activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc., esters with N-hydroxy compounds such as N,N-dimethylhydroxylamine, 1-hydroxy-2-(1H)-pyridone, N-hydroxysuccinimide, N-hydroxyphthalimide, 1-hydroxy-1H-benzotriazole, etc., among others.

These reactive derivatives can be selectively employed depending upon the type of compound, compound (III) is.

The preferred salt of such a reactive derivative of compound (III) includes-salts with various-bases, e.g. salts with alkali metals such as sodium, potassium, etc., salts with alkaline earth metals such as calcium, magnesium, etc., ammonium salts, salts with organic bases such as trimethylamine, triethylamine, pyridine, picoline, dicyclohexylamine, N,N-dibenzylethylenediamine, etc.

This reaction is generally conducted in water or an organic solvent. An organic solvent is preferably employed, e.g. alcohols such as methanol, ethanol, etc., acetone, dioxane, acetonitrile, chloroform, methylene chloride, ethylene chloride, tetrahydrofuran, ethyl acetate, N,N-dimethylformamide, and pyridine, although any other organic solvent that does not interfere with the reaction can be utilized. These common solvents can be used in admixture with water.

When compound (III) is used in the free form or in the form of a salt, this reaction is preferably conducted in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy- 1-chloroethylenes; trialkyl phosphites; ethyl polyphosphate; isopropyl polyphosphate; phosphorus oxychloride, diphenylphosphorylazide; thionyl chloride; oxalyl chloride; haloformic acid lower alkyl esters such as isopropyl chloroformate etc.; triphenylphosphine; 2-ethyl-7-hydroxybenzisoxazolium salts, 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; and Vilsmeier reagents prepared by reacting N,N'-dimethylformamide with thionyl chloride, phosgene, trichloromethyl chloroformate, or phosphorus oxychloride, etc.

The reaction may also be carried out in the presence of an inorganic or organic base such as alkali metal hydrogen carbonates, tri(lower)alkylamines, pyridine, N-(lower)alkylmorpholines, N,N-di(lower)alkylbenzylamines, etc. While the reaction temperature is not critical, the reaction is generally conducted under cooling to warming.

The starting compound (III) for process B can be produced by the following processes C through J.

Process C $$R^3-NH-\underset{\underset{(V)}{|}}{\overset{R^2}{\overset{|}{CH}}}-COOH + H_2N-\underset{\underset{(VI)}{|}}{\overset{R^1}{\overset{|}{CH}}}-COOL \longrightarrow$$

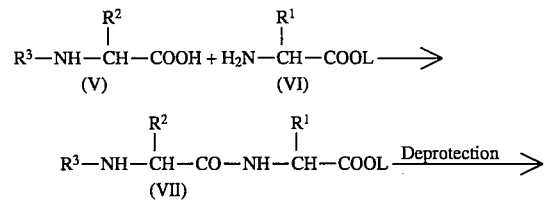

$$R^3-NH-\underset{|}{\overset{R^2}{\overset{|}{CH}}}-CO-NH-\underset{|}{\overset{R^1}{\overset{|}{CH}}}-COOH \quad \text{(III-1)}$$

wherein L represents a carboxyl-protecting group; other symbols have the meanings as defined hereinbefore.

The carboxyl-protecting group L that can be used includes various protective groups well known in the field of peptide synthesis, for example ester derivatives.

In this process, compound (V) or a reactive derivative of the carboxyl group thereof, or a salt thereof, is reacted with compound (VI) or a reactive derivative of the amino group thereof, or a salt thereof, to prepare compound (VII), which is then subjected to carboxyl-deprotection reaction to give compound (III-1).

The reaction of compound (V) or a reactive derivative of the carboxyl group thereof, or a salt thereof, with compound (VI) or a reactive derivative of the amino group thereof, or a salt thereof, can be carried out by the same procedure as described for process B.

The reaction for eliminating a protective group from the carboxyl function of compound (VII) can be carried out by any conventional carboxyl-deprotection procedures such as hydrolysis, reduction, and removal with a Lewis acid. Where the carboxyl-protecting group is an ester residue, it can be eliminated by hydrolysis or using a Lewis acid. The hydrolysis reaction is preferably conducted in the presence of a base or an acid.

The base that can be used with advantage includes inorganic bases such as alkali metal hydroxides (e.g. sodium hydroxide, potassium hydroxide, etc.),alkaline earth metal hydroxides (e.g. magnesium hydroxide, calcium hydroxide, etc.), alkali metal carbonates (e.g. sodium carbonate, potassium carbonate, etc.), alkaline earth metal carbonates (e.g. magnesium carbonate, calcium carbonate, etc.), alkali metal bicarbonates (e.g. sodium hydrogen carbonate, potassium hydrogen carbonate, etc.), alkali metal acetates (e.g. sodium acetate, potassium acetate, etc.), alkaline earth metal phosphates (e.g. magnesium phosphate, calcium phosphate, etc.), alkali metal hydrogen phosphates (e.g. disodium hydrogen phosphate, dipotassium hydrogen phosphate, etc.) and so on, and organic bases such as trialkylamines (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]non-5-ene, 1,8-diazabicyclo[5,4,0]-7-undecene and so on.

Hydrolysis with such a base is generally carried out in water, a hydrophilic organic solvent or a mixture of the solvents. The preferred acid includes organic acids such as formic acid and inorganic acids such as hydrochloric acid, hydrobromic acid, sulfuric acid and so on. This hydrolysis reaction is generally carried out in an organic solvent, water or a mixture of the solvents. The reaction temperature is not critical and can be selected according to the type of carboxyl-protecting group and the deprotection method used.

Deprotection with a Lewis acid can be achieved by reacting compound (VII) or its salt with a Lewis acid such as boron trihalides (e.g. boron trichloride, boron trifluoride, etc.), titanium tetrahalides (e.g. titanium tetrachloride, titanium tetrabromide, etc.), aluminum halides (e.g. aluminum chloride, aluminum bromide, etc.) and trihaloacetic acids (e.g. trichloroacetic acid, trifluoroacetic acid, etc.). This elimination reaction is preferably carried out in the presence of a cation trapping agent (e.g. anisole, phenol, etc.) and is usually carried out in a solvent such as a nitroalkane (e.g.

nitromethane, nitroethane, etc.), an alkylene halide (e.g. methylene chloride, ethylene chloride, etc.), diethyl ether, carbon disulfide or any other solvent that does not adversely affect the reaction. These solvents can be used as a mixture.

The reductive method of elimination can be followed with advantage for elimination of such protective groups as haloalkyl (e.g. 2-iodoethyl, 2,2,2-trichloroethyl, etc.) esters, aralkyl (e.g. benzyl etc.) esters and so on. This method includes reduction with a metal (e.g. zinc, zinc amalgam, etc.) or a chromium compound salt (e.g. chromium chloride, chromium acetate, etc.) in combination with an organic or inorganic acid (e.g. acetic acid, propionic acid, hydrochloric acid, etc.) and conventional catalytic reduction in the presence of a known metallic catalyst (e.g. palladium on carbon, Raney nickel, etc.), among others. While the reaction temperature is not critical, the reaction is usually carried out under cooling, at ambient temperature or under warming.

Process D

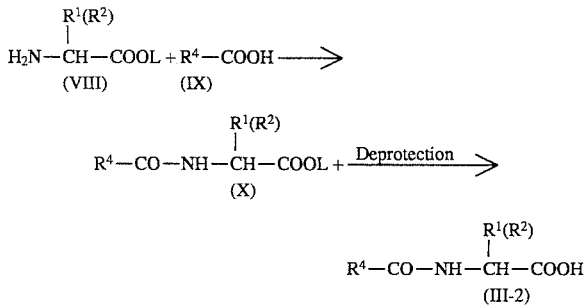

wherein all symbols have the meanings as defined hereinbefore.

In this process, compound (IX) or a reactive derivative of the carboxyl group thereof, or a salt thereof, is reacted with compound (VIII) or a reactive derivative of the amino group thereof, or a salt thereof, to prepare compound (X), which is then subjected to carboxyl-deprotection reaction to give compound (III-2). This reaction is conducted in the same manner as described for process C.

Process E

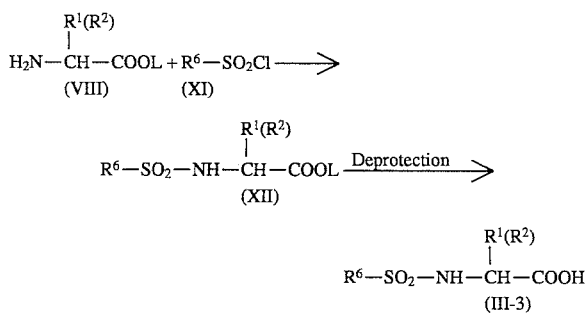

wherein all symbols have the meanings as defined hereinbefore.

In this process, compound (XI) or a salt thereof is reacted with compound (VIII) or a salt thereof to prepare compound (XII), which is then subjected to a carboxyl-deprotection reaction to give compound (III-3).

This reaction between (VIII) and (XI) is conducted in a suitable solvent. The solvent includes, among others, aromatic hydrocarbons such as benzene, toluene, xylene, etc., ethers such as dioxane, tetrahydrofuran, dimethoxyethane, etc., alcohols such as methanol, ethanol, propanol, etc., ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone, etc. and various mixtures thereof.

The reaction between (VIII) and (XI) is conducted in the presence of a suitable base, for example alkali metal salts such as sodium hydroxide, potassium hydroxide, potassium carbonate, sodium carbonate, sodium hydrogen carbonate, etc., amines such as pyridine, triethylamine, N,N-dimethylaniline, etc., sodium hydride, potassium hydride and so on. The amount of the base is preferably about 1–5 molar equivalents. This reaction is conducted generally at –20° C. –150° C. and preferably at about –10° C. –100° C. The compound (XII) thus obtained is then subjected to a deprotection reaction to produce compound (III-3). This deprotection reaction can be carried out in the same manner as the deprotection reaction in process C.

Process F

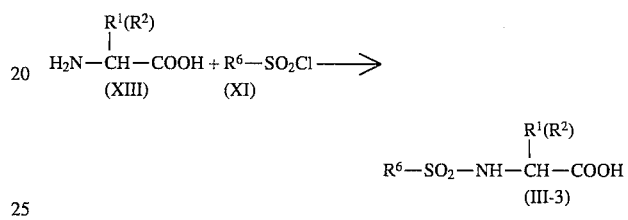

wherein all symbols have the meanings as defined hereinbefore.

In this process, compound (XIII) or a salt thereof is reacted with compound (XI) or a salt thereof to produce compound (III-3). This sulfonylation reaction is generally carried out by the Schotten Baumann method which comprises preparing an aqueous solution of the sodium salt of amino acid derivative (XIII), reacting it with compound (XI) and acidifying the reaction mixture.

Process G

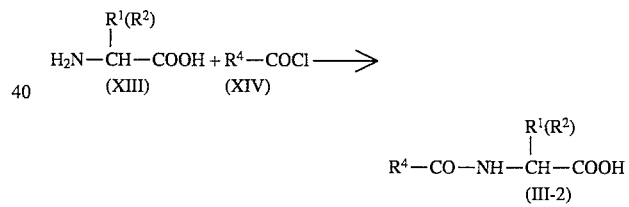

wherein all symbols have the meanings as defined hereinbefore.

In this process, compound (XIII) or a salt thereof is reacted with compound (XIV) or a salt thereof to produce compound (III-2). This acylation reaction is carried out in the same manner as in process F.

Process H

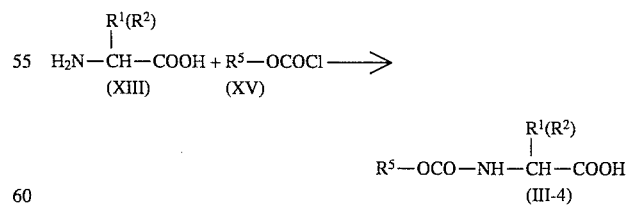

wherein all symbols have the meanings as defined hereinbefore.

In this process, compound (XIII) or a salt thereof is reacted with compound (XV) or a salt thereof to produce compound (III-4). This reaction is carried out in the same manner as in process G.

Process I

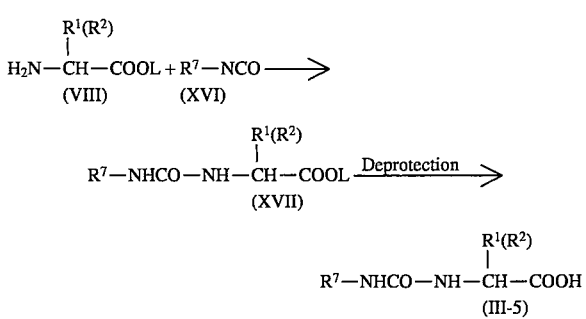

wherein all symbols have the meanings as defined hereinbefore.

In this process, compound (VIII) or a salt thereof is reacted with compound (XVI) to give compound (XVII), which is then subjected to a carboxyl-deprotection reaction to provide compound (III-5).

The reaction between compound (VIII) or a salt thereof and compound (XVI) is conducted in a suitable solvent. The solvent that can be used includes aromatic hydrocarbons such as benzene, toluene, xylene, etc., ethers such as dioxane, tetrahydrofuran, dimethoxyethane, etc., ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone, etc., and various mixtures thereof.

The proportion of compound (XVI) relative to compound (VIII) is preferably about 1 to 5 molar equivalents. This reaction is generally conducted at a temperature of −20° C.–150° C. preferably about −10– 100° C. The compound (XVII) thus obtained is then deprotected to give compound (III-5). This deprotection reaction can be carried out in the same manner as the deprotection reaction in process C.

Process J

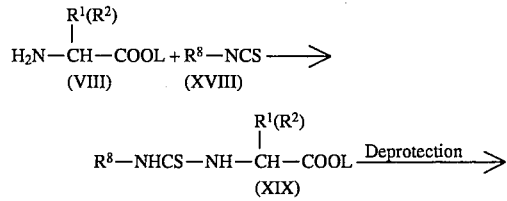

wherein all symbols have the meanings as defined hereinbefore.

In this process, compound (VIII) or a salt thereof is reacted with compound (XVIII) to give compound (XIX), which is then subjected to a carboxyl-deprotection reaction to provide compound (III-6). This process is carried out in the same manner as process I.

The starting compound (II) for process A can be produced by the following process as well.

Process K

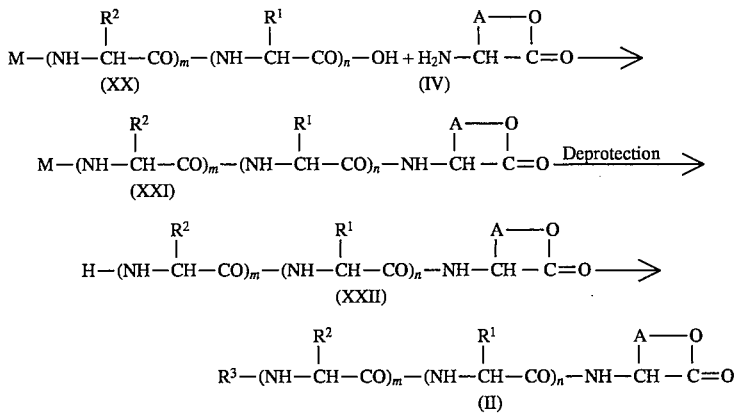

wherein M represents an amino-protecting group; all other symbols have the meanings as defined hereinbefore.

The amino-protecting group M may be any of various protective groups which are conventionally used in peptide synthesis and may for example be an oxycarbonyl derivative, which is preferably benzyloxycarbonyl.

In this process, compound (XX) or a reactive derivative of the carboxyl group thereof, or a salt thereof, is reacted with compound (IV) or a reactive derivative of the amino group thereof, or a salt thereof, to prepare compound (XXI), which is then subjected to an amino-deprotection reaction to give compound (XXII). This reaction between compound (XX) or a reactive derivative of the carboxyl group thereof, or a salt thereof, and compound (IV) or a reactive derivative of the amino group thereof, or a salt thereof, can be carried out in the same manner as in process B.

The amino-deprotection of compound (XXI) can be carried out by the conventional manner for eliminating an amino-protecting group. Elimination of benzyloxycarbonyl, for instance, can be effected by catalytic hydrogenation in the presence of the common metal catalyst (e.g. palladium-on-carbon, Raney nickel, etc.) The reaction temperature is not critical. Thus, the reaction can be generally carried out under cooling, at room temperature or under warming, unless an undesirable reaction is caused. Compound (XXII) is then acylated in a manner analogous to the reaction between compounds (VIII) and (IX) in process D or the reaction between compounds (XIII) and (XIV) in process G, sulfonylated in a manner analogous to the reaction between compounds (VIII) and (XI) in process E, oxycarbonylated in a manner analogous to the reaction between compounds (XIII) and (XV) in process H, carbamoylated in a manner analogous to the reaction between compounds (VIII) and (XVI) in process I, or thiocarbamoylated in a manner analogous to the reaction between compounds (VIII) and (XVIII) in process J to provide the corresponding compound (II).

Compounds of general formula (I) wherein B is an acyl group can be produced by process L.

Process L

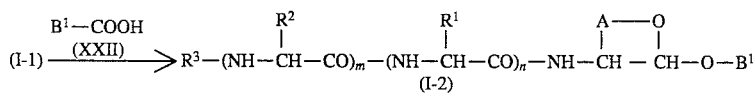

wherein $B^1$ represents an acyl group; all other symbols have the meanings as defined hereinbefore.

As the acyl group $B^1$, the acyl groups mentioned for B can be used.

In this process, the lactol derivative (I-1) is acylated to compound (I-2).

Thus, (I-2) is produced by reacting compound (XXII) or a reactive derivative of the carboxyl group thereof with compound (I-1). The preferred reactive derivative of the carboxyl group of compound (XXII) includes acid halides, acid anhydrides, activated amides, activated esters and so on. Preferred examples of such reactive derivative are acid chloride; acid azide; mixed acid anhydrides with various acids such as substituted phosphoric acids, e.g. dialkylphosphoric acid, phenylphosphoric acid, diphenylphosphoric acid, dibenzylphosphoric acid, halophosphoric acids, etc., dialkylphosphorous acids, sulfurous acid, thiosulfuric acid, sulfuric acid, sulfonic acids such as methanesulfonic acid etc., aliphatic carboxylic acids such as acetic acid, propionic acid, lactic acid, isolactic acid, pivalic acid, pentanoic acid, isopentanoic acid, trichloroacetic acid, etc., aromatic carboxylic acids such as benzoic acid etc.; symmetric acid anhydride; activated amides with imidazole, 4-substituted imidazoles, dimethylpyrazole, triazole, tetrazole, etc.; activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc., esters with N-hydroxy compounds such as N,N-dimethylhydroxamine, 1-hydroxy-2-(1H)-pyridone, N-hydroxysuccinimide, N-hydroxyphthalimide, 1-hydroxy-1H-benzotriazole, etc., among others. These reactive derivatives can be selectively employed. This reaction is generally conducted in water or an organic solvent, which is preferably employed, e.g. alcohols such as methanol, ethanol, etc., acetone, dioxane, acetonitrile, chloroform, methylene chloride, ethylene chloride, tetrahydrofuran, ethyl acetate, N,N-dimethylformamide, and pyridine, although any other organic solvent that does not interfere with the reaction can be utilized. These common solvents can be used in admixture with water. When compound (XXII) is used in the free form or in the form of a salt, this reaction is preferably conducted in the presence of a conventional condensing agent such as N,N'-dicyclohexyl carbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide, N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy- 1-chloroethylenes; trialkyl phosphites; ethyl polyphosphate; isopropyl polyphosphate; phosphorus oxychloride, diphenylphosphorylazide; thionyl chloride; oxalyl chloride; haloformic acid lower alkyl esters such as ethyl chloroformate, isopropyl chloroformate etc.; triphenylphosphine; 2-ethyl-7-hydroxybenzisoxazolium salt, 2-ethyl-5-(m-sulfophenyl)isoxazolium hydroxide internal salt; N-hydroxybenzotriazole; 1-(p-chlorobenzenesulfonyloxy)-6-chloro- 1H-benzotriazole; and Vilsmeier reagents prepared by reacting N,N'-dimethylformamide with thionyl chloride, phosgene, trichloromethyl chloroformate, or phosphorus oxychloride, etc. The reaction may also be carried out in the presence of an inorganic or organic base such as alkali metal hydrogen carbonates, tri(lower)alkylamines, pyridine, N-(lower)alkylmorpholines, N,N-di(lower)alkylbenzylamines, etc. While the reaction temperature is not critical, the reaction is generally conducted under cooling to warming.

Compounds of general formula (I) wherein B represents an alkyl group can be produced by process M.

Process M

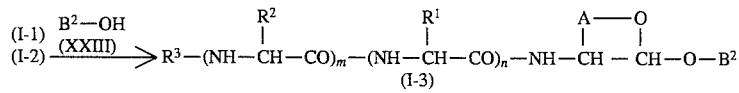

wherein $B^2$ represents an alkyl group; other symbols have the meanings as defined hereinbefore.

The alkyl group $B^2$ may be any of the species mentioned for the alkyl group B.

In this process, compound (I-1) or (I-2) is reacted with compound (XXIII) in the presence of an acid to provide compound (I-3). This reaction is carried out using a large excess of (XXIII) and adding 0.001–1.0 molar equivalents, based on compound (I-1) or (I-2), of a mineral acid, such as hydrochloric acid, sulfuric acid, nitric acid, hydrobromic acid, etc., p-toluenesulfonic acid or the like. While the reaction temperature is not critical, the reaction is preferably conducted at 0°–50° C. for 0.5–100 hours, particularly for 0.5–10 hours.

The compound of general formula (I-1) can also be produced from compound (I-3) by process N or from compound (I-2) by process 0.

Process N (I-3)→(I-1)

In this process, compound (I-3) is treated with an acid in a hydrous solvent. The hydrous solvent includes mixtures of water with alcohols such as methanol, ethanol, propanol, etc., ethers such as ethyl ether, tetrahydrofuran, dioxane, etc., acetonitrile, acetone, 2-butanone, N,N-dimethylformamide, dimethyl sulfoxide and so on. The acid includes hydrochloric acid, sulfuric acid, nitric acid, hydrobromic acid, acetic acid, p-toluenesulfonic acid and so on. The amount of the acid relative to compound (I-3) is 0.001–1.0 molar equivalents. While the reaction temperature is not critical, the reaction is preferably carried out at 0°–50° C. for 0.5–100 hours, particularly for 0.5°–10 hours.

Process O

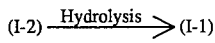

This hydrolysis reaction can be carried out in a hydrous solvent in the presence of an acid or a base by conventional means. The hydrous solvent includes mixtures of water with alcohols such as methanol, ethanol, propanol, etc., ethers such as ethyl ether, tetrahydrofuran, dioxane, etc., acetonitrile, acetone, 2-butanone, N,N-dimethylformamide, dimethyl sulfoxide and so on. The acid includes hydrochloric acid, sulfuric acid, nitric acid, hydrobromic acid, acetic acid, p-toluenesulfonic acid and so on. The amount of the acid relative to compound (I-2) is 0.001–1.0 molar equivalents. While the reaction temperature is not critical, the reaction is preferably carried out at 0°–100° C. for 0.5°–100° C. hours, particularly for 0.5–10 hours. The base includes potassium hydroxide, sodium hydroxide, lithium hydroxide, potassium carbonate, sodium carbonate and so on. The amount of the base relative to compound (I-2) is 1–5 molar equivalents. The reaction temperature in this case is not critical, either, but the reaction is preferably carried out at 0°–100° C. for 0.5–100 hours, particularly for 0.5°–10 hours.

The compound of general formula (I-5) can be produced from compound (I-4) by process P, too.

Process P

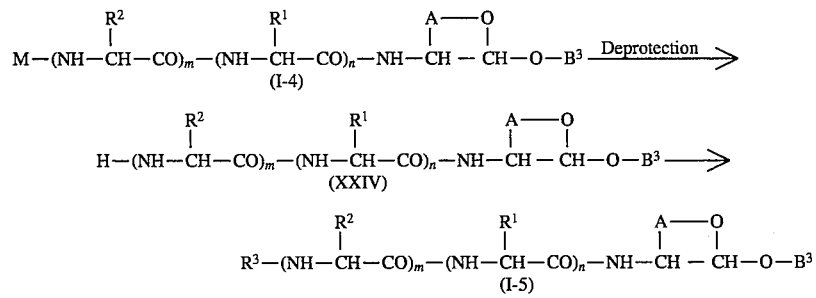

wherein $B^3$ represents an acyl group or an alkyl group; other symbols have the meanings as defined hereinbefore.

The acyl or alkyl group $B^3$ may be any of the species mentioned for the acyl or alkyl group B.

In this process, compound (I-4) is deprotected, in the same manner as the conversion of (XXI) to (XXII) in process K, to provide compound (XXIV). This compound (XXIV) is further treated in the same manner as for conversion of (XXII) to (II) in process K to provide compound (I-5).

The starting compound (I-4) for process P can be produced by process Q, too.

Process Q

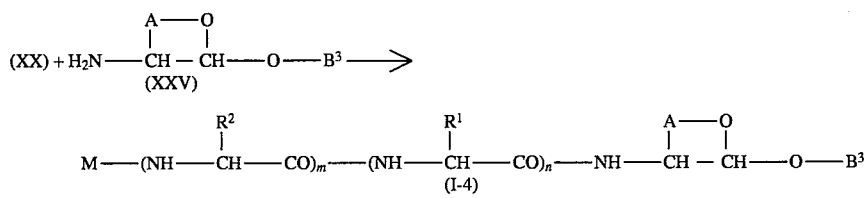

wherein each symbol has the meaning as defined hereinbefore.

This process is conducted in the same manner as process B.

The compound of general formula (II) can be produced by process R, too.

Process R

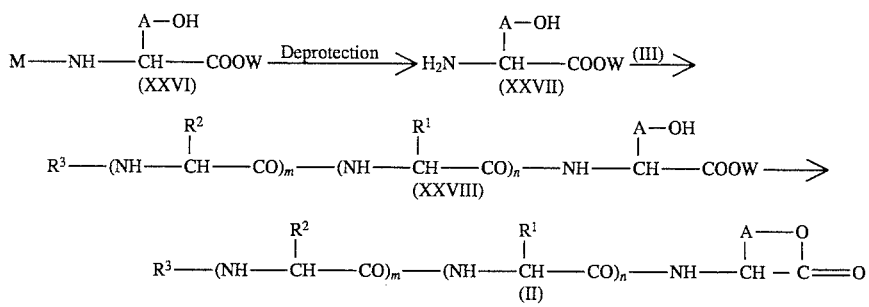

wherein W represents a lower alkyl group; other symbols have the meanings as defined hereinbefore.

The deprotecting reaction of compound (XXVI) can be carried out in the same manner as the conversion of compound (XXI) to compound (XXII) in process K. The reaction between compounds (XXVII) and (III) is carried out in the same manner as process B. The lactonization of compound (XXVIII) comprises heating compound (XXVIII) in a solvent in the presence of an acid in a manner known in the art. The solvent that can be used includes alcohols such as methanol, ethanol, propanol, etc., aromatic hydrocarbons such as benzene, toluene, xylene, etc., ethers such as ethyl ether, tetrahydrofuran, dioxane, etc., acetonitrile, acetone, 2-butanone, N,N-dimethylformamide, dimethyl sulfoxide and so on. Preferred are aromatic hydrocarbons such as benzene, toluene, xylene and so on. The acid includes hydrochloric acid, sulfuric acid, nitric acid, hydrobromic acid, acetic acid, p-toluenesulfonic acid and so on. The amount of the acid relative to compound (XXVIII) is 0.001–1.0 molar equivalents. While the reaction temperature is not critical, the reaction is preferably carried out at 0°–150° C. for 0.5–100 hours, particularly for 0.5–10 hours.

The compound of general formula (IV) can be produced by process S.

Process S

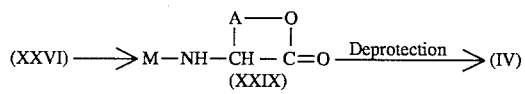

wherein each symbol has the meaning as defined hereinbefore.

The lactonization of compound (XXVI) can be accomplished in the same manner as the conversion of compound (XXVIII) to compound (II) in process R. The deprotecting reaction of compound (XXIX) can be carried out in the same manner as the conversion of (XXI) to (XXII) in process K.

The compound of general formula (XXV) can be produced by process T.

Process T (XXIX) ——>

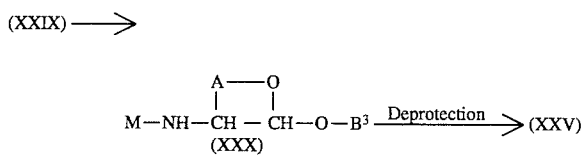

wherein each symbol has the meaning as defined hereinbefore.

The reaction from compound (XXIX) to compound (XXX) is carried out in the sequence of process A-process M or in the sequence of process A-process L. The deprotecting reaction of compound (XXX) is carried out in the same manner as the conversion of (XXI) to (XXII) in process K.

The compound of general formula (Ia) mentioned above can be produced in accordance with the method for producing the compound of general formula (I-1), wherein B is hydrogen in the formula (Ia) mentioned above, the formula (I-2), wherein B is an acyl group in the formula (Ia) mentioned above or the formula (I-3), wherein B is an alkyl group in the formula (Ia) mentioned above, in formulas of which at least m or n is 1.

The compound of general formula (IIa) mentioned above can be produced in accordance with the method for producing the compound of general formula (II), wherein at least m or n is 1.

The object compound (Ia) or (Ib) of this invention can be formulated with a pharmaceutically acceptable carrier and administered orally or otherwise in a variety of solid dosage forms such as tablets, capsules, granules, powders, etc. or in a variety of liquid dosage forms such as syrups, injections and so on.

The pharmaceutically acceptable carrier that can be used includes a variety of organic and inorganic carriers which are conventionally used in pharmaceutical production. The carrier mentioned above may function as an excipient, lubricant, binder, disintegrator or other additive in solid dosage forms or as a solvent, solubilizer, suspending agent, isotonizing agent, buffer, or soothing agent (local anesthetic) in liquid dosage forms. Where necessary, various pharmaceutical additives such as preservatives, antioxidants, coloring agents, sweeteners, etc. can also be incorporated.

The excipient includes, as preferred examples, lactose, sucrose, D-mannitol, starch, crystalline cellulose, light silicic anhydride and so on.

The lubricant includes, as preferred examples, magnesium stearate, calcium stearate, talc, colloidal silica and so on.

The binder includes, as preferred examples, crystalline cellulose, sucrose, D-mannitol, dextrin, hydroxypropylcellulose, hydroxypropylmethylcellulose, polyvinylpyrrolidone and so on.

The disintegrator includes, as preferred examples, starch, carboxymethylcellulose, carboxymethylcellulose calcium, croscarmellose sodium, carboxymethylstarch sodium and so on.

Among preferred examples of the solvent are water for injection, alcohol, propylene glycol, macrogols, sesame oil, corn oil and so on.

The solubilizer includes, as preferred examples, polyethylene glycol, propylene glycol, D-mannitol, benzyl benzoate, ethanol, trisaminomethane, cholesterol, triethanolamine, sodium carbonate, sodium citrate and so on.

The preferred suspending agent includes various surfactants such as stearyltriethanolamine, sodium lauryl sulfate, laurylaminopropionic acid, lecithin, benzalkonium chloride, benzethonium chloride, glyceryl monostearate, etc.; hydrophilic polymers such as polyvinyl alcohol, polyvinyl pyrrolidone, carboxymethylcellulose sodium, methylcellulose, hydroxymethylcellulose, hydroxyethylcellulose, hydroxypropylcellulose and so on.

The isotonizing agent includes, as preferred species, sodium chloride, glycerol, D-mannitol and so on. The buffer includes, as preferred species, various buffer solutions such as phosphate buffer, acetate buffer, carbonate buffer and citrate buffer solutions. A preferred example of the soothing agent is benzyl alcohol. The preservative includes, as preferred species, p-hydroxybenzoic acid esters, chlorobutanol, benzyl alcohol, phenethyl alcohol, dehydroacetic acid, sorbic acid and so on. The antioxidant includes sulfites and ascorbic acid, to mention just a few preferred examples.

The compound (Ia) or (Ib) of this invention is characterized not only by potent cathepsin L inhibitory activity but also by potent bone resorption inhibitory activity. Moreover, its toxic potential is low. For example, oral administration of the compounds in Example 60 and Example 94 at a dose of 500 mg/kg, respectively, to mice killed no test animals. Therefore, the compound (Ia) or (Ib) of this invention can be used in the prophylaxis and therapy of osteoporosis in mammalian animals (e.g. mouse, rat, rabbit, dog, cat, cattle, swine and man).

For use as a prophylactic/therapeutic drug for osteoporosis, compound (Ia) or (Ib) or a salt thereof can be administered in a daily dose, per adult human, of 1–1000 mg or preferably 10–600 mg.

The pharmaceutical composition of this invention exhibits strong cathepsin L and bone resorption inhibitory actions and acts directly on the bone to improve the metabolism of the bone.

Furthermore, compound (Ia) or (Ib) and its salt are only sparingly toxic and, therefore, of value as prophylactic/therapeutic agents for osteoporosis.

Since the compound (Ia) or (Ib) of the present invention has a promotion activity of calcification of osteoblasts i.e. bone-inducing activity, it is utilized as medicines for mammals (such as humans, mice, rats, cats, dogs, rabbits, cattle and pigs), and can be used, for example, as bone-inducing agents when the bones are repaired or transplanted. The compound (Ia) or (Ib) of the present invention can also be used for a treatment of non-connective fracture, a fixation of artificial arthrosis and a repair of an alveolar bone. For example, the compound (Ia) or (Ib) of the present invention can be allowed to be adhered to or contained in artificial bones made of metals, ceramics or polymers. The artificial bones preferably have porous surfaces so that the compound (Ia) or (Ib) are released in the organism tissues in transplanting the artificial bones to bone defective portions.

The compound (Ia) or (Ib) of the present invention are dispersed in appropriate dispersing agents, binders and diluents, etc. such as collagen, physiological salines, citric acid solutions, acetic acid solutions, hydroxyapatite, fibrin and mixed solutions thereof. The artificial bones can be coated or impregnated with the resulting dispersions, and then dried, thereby allowing the compound (Ia) or (Ib) to be adhered to or contained in the artificial bones. Such artificial bones are transplanted to bone-defective portions, and firmly fixed thereto. Fixing agents for artificial bones can be prepared by mixing the compound (Ia) or (Ib), active ingredients, with physiologically acceptable dispersing media, binders, diluents, other ingredients effective for osteoanagenesis (for example, calcium), etc. The fixing agents for artificial bones can also be used so as to fill gaps between the artificial bones transplanted to bone-defective portions and the bone-defective portions, without allowing the fixing agents to be adhered to or contained in the artificial bones.

The compound (Ia) or (Ib) of the present invention are low in toxicity and can be safely used. For example, they can be topically given in an amount of 0.1 to 100 mg, preferably 0.1 to 10 mg, to bone-defective portions or -decreased portions.

Actions

The following experiment example is intended to illustrate the pharmacologic action of compound (Ia) or (Ib).

Experiment Example 1

(human cathepsin L inhibitory action)

The recombinant human cathepsin L obtained by the procedure described in Example 8 of the specification of EPC 931098792 (European Publication No. 0576953 A2) (which is incorporated herein by reference) was diluted to 1 µg/ml with a diluent (0.1% Brij35, Sigma). This diluted enzyme solution was admixed with 46 µl of said diluent, 2 µl of 0.1M DTT and 25 µl of an activator/buffer (340 mM sodium acetate, 60 mM acetic acid, 4 mM EDTA disodium, pH 5.5). Then, 1 µl of a solution of the test compound in dimethyl sulfoxide (DMSO) ($10^{-2}$M) and 25 µl of 20 µM Z-phe-Arg-NMec (substrate solution) were added. The mixture was incubated at 30° C. for 10 minutes, after which 100 µl of a reaction stopper (100 mM sodium monochloroacetate, 30 mM sodium acetate, pH 4.3) was added. This reaction was carried out on a 96-well Fluoroplate (Labosystems).

After termination of the reaction, the intensity of fluorescence of liberated aminomethylcoumarin at 450 nm was measured at an excitation wavelength of 365 nm. As a blank experiment, 1 µl of DMSO not containing the test compound was added and the intensity of fluorescence after the reaction was taken as 100% activity. For a sample showing a residual activity of 10% or less, a further diluted solution was used to determine the residual activity by the same procedure as above. Then, $IC_{50}$ values were calculated. The results are presented in Table 1.

TABLE 1

| Compound (Example No.) | Cathepsin L-inhibitory activity [$IC_{50}$ (M)] |
| --- | --- |
| 1 | $3.0 \times 10^{-8}$ |
| 4 | $5.7 \times 10^{-8}$ |
| 5 | $8.0 \times 10^{-9}$ |
| 6 | $3.0 \times 10^{-8}$ |
| 12 | $3.2 \times 10^{-8}$ |
| 14 | $9.4 \times 10^{-9}$ |
| 17 | $6.9 \times 10^{-9}$ |
| 23 | $2.8 \times 10^{-8}$ |
| 25 | $4.5 \times 10^{-7}$ |
| 38 | $5.2 \times 10^{-8}$ |
| 42 | $2.9 \times 10^{-8}$ |
| 62 | $8.7 \times 10^{-7}$ |
| 64 | $6.9 \times 10^{-7}$ |
| 89 | $1.9 \times 10^{-7}$ |

Experiment Example 2

(bone resorption inhibitory action)

Bone resorption inhibitory activity was assayed by the method of Raisz [J. Clin. Invest. 44, 103–116 (1965) which is incorporated herein by reference]. Thus, a Sprague-Dawley rat on day 18 of gestation was subcutaneously dosed with 50 µCi of $^{45}$Ca (an isotope of calcium, dissolved in $CaCl_2$).

The following day, the abdomen was opened and the fetuses were aseptically extracted. Under the dissecting microscope, the bilateral antebrachial bones (radii, cubiti) were separated from the carcass and the connective tissues and cartilages were removed as far as possible to prepare bone culture specimens. Each of these bone specimens was put in 0.6 ml of BGJb medium (Fitton-Jackson modification; GIBCO Laboratories, USA) supplemented with bovine serum albumin (final concentration 2 mg/ml) and incubated at 37° C. for 24 hours. This bone was further cultured in the same medium containing the test compound (final concentration 10 μM or 30 μM) for 2 days. The percent ratio (%) of $^{45}Ca$ released from the bone to the medium was calculated from the radioactivity count in the medium and that in the bone by means of the following equation.

Percent ratio of $^{45}Ca$ released from bone to medium =

$$\frac{^{45}Ca \text{ count in medium}}{^{45}Ca \text{ count in medium} + ^{45}Ca \text{ count in bone}} \times 100$$

As a control group, the bones from a fetus of the same litter were similarly cultured for 2 days. The mean ± standard deviation was calculated for 5 bone pieces per group and the percentage (%) of this value relative to the value of the control group was calculated. The results are shown in Table 2.

TABLE 2

| Compound (Example No.) | Concentration of compound (μM) | Bone resorption Inhibitory Activity [$^{45}Ca$ release (Percent to control)] |
|---|---|---|
| 12 | 10 | 64** |
| 15 | 10 | 26*** |
| 16 | 10 | 77*** |
| 21 | 10 | 67** |
| 25 | 10 | 75** |
| 29 | 30 | 67** |
| 32 | 30 | 77* |
| 35 | 10 | 82* |
| 73 | 10 | 79* |
| 74 | 10 | 78* |

*, $p<0.05$; , $p<0.01$; *, $p<0.001$ (vs. control, Student's t-test)

This invention is hereinafter described in detail by means of the following reference examples and examples. The optical rotation in the following reference examples and examples was measured at room temperature (22°–25° C).

REFERENCE EXAMPLE 1

A mixture of N-benzyloxycarbonyl-(L)-homoserine (9.0 g), 1-hydroxybenzotriazole (HOBt) (5.4 g) and N,N-dimethylformamide (DMF) (50 ml) was provided and 1-ethyl-3-(3-dimethylaminopropyl)carbodiimide hydrochloride (WSCD.HCl) (7.5 g) was added to the mixture under ice-cooling. The whole mixture was stirred at room temperature for 14 hours. The reaction mixture was then poured into water and extracted with ethyl acetate. The ethyl acetate layer was washed with 1% aqueous citric acid, water, saturated aqueous sodium hydrogen carbonate and saturated aqueous sodium chloride in the order mentioned and dried over $MgSO_4$ and the solvent was distilled off, whereby (S)-3-(N-benzyloxycarbonylamino)tetrahydrofuran-2-one (7.0 g, 84.3%) was obtained. This product was recrystallized from dichloromethane-isopropyl ether. Colorless needles, m.p. 129°–130° C. Optical rotation $[\alpha]_D$–0.5° (C=0.52, $CHCl_3$).

REFERENCE EXAMPLE 2

(S)-3-(N-Benzyloxycarbonylamino)tetrahydrofuran-2-one (1.56 g) was dissolved in ethanol (100 ml) and following addition of palladium-on-carbon (5%, 0.5 g), the catalytic hydrogenation was carried out at room temperature and atmospheric pressure. The catalyst was then filtered off and the filtrate was concentrated under reduced pressure. The residue was dissolved in N,N-dimethylformamide (DMF) (20 ml), and N-(tert-butoxycarbonyl)-(L)-phenylalanine (Boc-Phe-OH) (1.94 g) and 1-hydroxybenzotriazole (HOBt)(1.1 g) were added. Then, 1-ethyl-3-(3-dimethylaminopropyl)carbodiimide hydrochloride (WSCD.HCl) (1.5 g) was added under ice-cooling and the whole mixture was stirred at room temperature for 14 hours. The reaction mixture was then poured into ice-water and extracted with ethyl acetate. The ethyl acetate layer was washed with 10% aqueous citric acid, water, saturated aqueous sodium hydrogen carbonate and saturated aqueous sodium chloride in the order mentioned and dried ($MgSO_4$) and the solvent was distilled off to give (S)-3-[(N-tert-butoxycarbonyl-(L)-phenylalanyl) amino]tetrahydrofuran-2-one (chemical formula below) (1.8 g, 78.3%). This product was recrystallized from dichloromethaneisopropyl ether. Colorless crystals, m.p. 132°–133° C. Optical rotation $[\alpha]_D$–9.1° (C=0.51, $CHCl_3$).

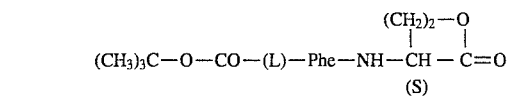

REFERENCE EXAMPLE 3–7

The compounds listed in Table 3 were synthesized by the same procedure as described in Reference Example 2.

TABLE 3

R—NH—CH—C=O with (CH₂)₂—O ring (S)

| Reference Example No. | R | Melting point (°C.) | Recrystallization solvent | Optical rotation $[\alpha]_D$ (conc./solvent) |
|---|---|---|---|---|
| 3 | $(PhCH_2)_2CHCO-$ | 150–151 | Ethyl acetate/hexane/isopropyl ether | –11.0° (c = 0.53, $CHCl_3$) |
| 4 | Cbz—(L)—Ile— | 178–179 | Chloroform/isopropyl ether | –12.7° |

TABLE 3-continued $$R-NH-CH-C=O$$
with $(CH_2)_2-O$ ring, (S)

| Reference Example No. | R | Melting point (°C.) | Recrystallization solvent | Optical rotation $[\alpha]_D$ (conc./solvent) |
|---|---|---|---|---|
| 5 | 1-Np—SO$_2$—(L)—Ile— | 203–204 | Dichloromethane/methanol/isopropyl ether | −24.1° (c = 0.51, CHCl$_3$) |
| 6 | Cbz—(L)—Phe— | 115–117 | Ethyl acetate/isopropyl ether | −7.2° (c = 0.98, CHCl$_3$) |
| 7 | Cbz—(L)—Val— | 179–180 | Dichloromethane/methanol/isopropyl ether | −10.1° (c = 0.5, CHCl$_3$) |

Ph: phenyl, Cbz: Benzyloxycarbonyl, 1-Np: 1-naphthyl, Ile: isoleucine, Val: valine, Phe: phenylalanine (first entry row shows c = 0.52, CHCl$_3$ for Example 5)

REFERENCE EXAMPLE 8

(S)-3-[[N-Benzyloxycarbonyl-(L)-phenylalanyl]amino] tetrahydrofuran-2-one (1.5 g) was dissolved in tetrahydrofuran (35 ml) followed by addition of palladium-on-carbon (5%, 0.8 g) and the catalytic hydrogenation was carried out at room temperature and atmospheric pressure. The catalyst was then filtered off and the filtrate was concentrated under reduced pressure. The residue was dissolved in N,N-dimethylformamide (DMF) (35 ml). Then, valproic acid [(C$_3$H$_7$)$_2$CHCOOH](0.622 g) and 1-hydroxybenzotriazole (HOBt) (0.66 g) were added, after which 1-ethyl-3-(3-dimethylaminopropyl)carbodiimide hydrochloride (WSCD.HCl) (0.902 g) was added under ice-cooling and the whole mixture was stirred at room temperature for 14 hours. The reaction mixture was then poured into ice-water and extracted with ethyl acetate. The ethyl acetate layer was washed with 10% aqueous citric acid, water, saturated aqueous sodium hydrogen carbonate and saturated aqueous sodium chloride in the order mentioned and dried (MgSO$_4$) and the solvent was distilled off to give (S)-3-[[N-valproyl-(L)-phenylalanyl]amino]tetrahydrofuran-2-one (chemical formula below) (0.55 g, 38%). This product was recrysalized from dichloromethane-ether. Colorless prisms, m.p. 203°–205° C. Optical rotation $[\alpha]_D$–39.3° (c=0.52, CHCl$_3$).

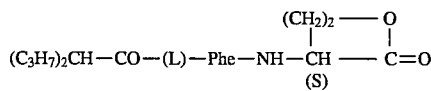

REFERENCE EXAMPLE 9

(S )-3-[[N-Benzyloxycarbonyl-(L)-phenylalanyl ]amino] tetrahydrofuran-2-one (1.3 g) was dissolved in teterahydrofuran (35 ml )-ethanol (10 ml ) and following addition of palladium-on-carbon (5%, 0.847 g), the catalytic hydrogenation was carried out at ambient temperature and atmospheric pressure. The catalyst was then filtered off and the filtrate was concentrated under reduced pressure. The oily residue was dissolved in N,N-dimethylformamide (DMF) (35 ml) followed by addition of 1-naphthalenesulfonyl chloride (0.847 g) and the mixture was cooled at 0° C. Then, 4-dimethylaminopyridine (DMAP) (0.478 g) was added and the mixture was stirred at 0° C. for 1.5 hours. The reaction mixture was then poured into water and extracted with ethyl acetate. The ethyl acetate layer was washed with 10% aqueous citric acid, water, saturated aqueous sodium hydrogen carbonate and saturated aqueous sodium chloride in the order mentioned and dried ((MgSO$_4$) and the solvent was distilled off. The residue was chromatographed on a silica gel column and elution was carried out with chloroform-ethyl acetate (1:1, v/v). From the eluate was obtained (S)-3-[[N-(1-naphthalenesulfonyl)-(L)-phenylalanyl]amino] tetrahydrofuran-2-one (chemical formula below) (0.6 g, 40%). As recrystallized from ethyl acetate-isopropyl ether, colorless prisms, m.p. 93°–94° C. optical rotation $[\alpha]_D$–117 3° (C=0.52, CHCl$_3$)

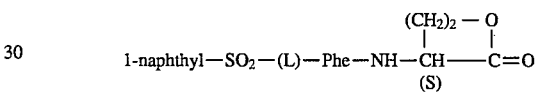

REFERENCE EXAMPLE 10

(S)-3-[[N-Benzyloxycarbonyl-(L)-leucyl]amino]tetrahydrofuran-2-one (1.5 g) was dissolved in tetrahydrofuran (150 ml) and following addition of palladium-on-carbon (5%, 0.2 g), the catalytic hydrogenation was carried out at ambient temperature and atmospheric pressure. The catalyst was then filtered off and α-naphthyl isocyanate (0.76 g) was added to the filtrate. This mixture was stirred at room temperature for 14 hours. The reaction mixture was then concentrated under reduced pressure to give (S)-3-[[N-(1-naphthylcarbamoyl)-(L)-leucyl]amino]tetrahydrofuran-2-one (chemical formula below) (1.05 g, 63%). As recrystallized from chloroform-methanol-isopropyl ether, colorless crystals, m.p. 213°–214° C., optical rotation $[\alpha]_D$–25.6° (C=0.19, CH$_3$OH )

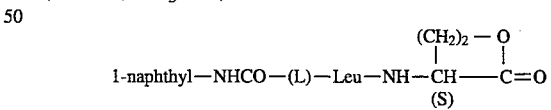

REFERENCE EXAMPLE 11

In benzene (100 ml) was dissolved tert-butyl (S)-2-(N-benzyloxycarbonylamino)-5-hydroxyvalerate [synthesized by the method described in the Journal of Organic Chemistry, 55, 1711 (1990)](5.1 g) and following addition of p-toluenesulfonic acid (0.05 g), the mixture was stirred under reflux for 1 hour. This reaction mixture was diluted with ethyl acetate (100 ml) and washed with water, saturated aqueous sodium hydrogen carbonate and saturated aqueous sodium chloride in the order mentioned. After drying (MgSO$_4$), the solvent was distilled off. The residue was chromatographed on a silica gel column and elution was carried out with ethyl acetate-hexane (1:2, v/v). From the eluate was obtained (S)-3-(N-benzyloxycarbonylamino)-2-oxotetrahydropyran (2.0 g, 51%) as an oil. NMR (δ ppm in CDCl$_3$): 1.54–1.74 (1H, m), 1.96–2.10 (2H, m), 2.55–2.72 (1H, m), 4.36 (2H, t, J=6.2 Hz), 4.37–4.50 (1H, m), 5.13 (2H, s), 5.62 (1H, broad), 7.34–7.40 (5H, m). Optical rotation [α]$_D$+51.5° (C=0.98, CHCl$_3$)

REFERENCE EXAMPLE 12

Methyl (S)-2-(N-benzyloxycarbonylamino)-5-hydroxyvalerate (5.0 g) was dissolved in tetrahydrofuran (150 ml) and following addition of palladium-on-carbon (5%, 1.0 g), the catalytic hydrogenation was carried out at ambient temperature and atmospheric pressure. The catalyst was then filtered off and the filtrate was concentrated under reduced pressure. The oily residue was dissolved in N,N-dimethylformamide (DMF) (20 ml) followed by addition of N-benzyloxycarbonyl-(L)-phenylalanine (Cbz-Phe-0H) (5.9 g) and 1-hydroxybenzotriazole (HOBt) (3.0 g) and the mixture was cooled at 0° C. Then, 1-ethyl-3-(3-dimethylaminopropyl)carbodiimide hydrochloride (WSCD.HCl) (4.1 g) was added and the mixture was stirred at 0° C. for 1 hour and then at room temperature for 15 hours. The reaction mixture was poured into ice-water and extracted with ethyl acetate. The ethyl acetate layer was washed with 10% aqueous citric acid, water, saturated aqueous sodium hydrogen carbonate and saturated aqueous sodium chloride in the order mentioned and dried (MgSO$_4$) and the solvent was distilled off. The residue was chromatographed on a silica gel column and elution was carried out with ethyl acetate-hexane (1:1, v/v). From the eluate was obtained methyl (S)-2-[[N-benzyloxycarbonyl-(L)-phenylalanyl]amino]-5-hydroxyvalerate (chemical formula below) (3.0 g, 40%). As recrystallized from dichloromethane-hexane, colorless needles, m.p. 155°–157° C., optical rotation [α]$_D$+5.4° (C=0.50, CHCl$_3$)

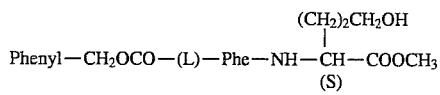

REFERENCE EXAMPLE 13

In benzene (100 ml) was dissolved methyl (S)-2-[[N-benzyloxycarbonyl-(L)-phenylalanyl]amino]-5-hydroxyvalerate (2.85 g) followed by addition of p-toluenesulfonic acid (0.09 g), and the mixture was stirred under reflux for 1 hour. The reaction mixture was concentrated under reduced pressure to provide (S)-3-[[N-benzyloxycarbonyl-(L)-phenylalanyl]amino]-2-oxotetrahydropyran (chemical formula below) (2.0 g, 77%) m p 167°–169° C. optical rotation [α]$_D$+43.6° (c=0.50, CHCl$_3$)

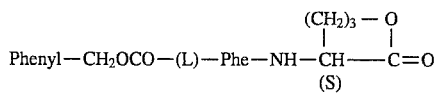

REFERENCE EXAMPLE 14

In substantially the same manner as Reference Example 12, methyl (S)-2-[[N-benzyloxycarbonyl-(L)-leucyl]amino]-5-hydroxyvalerate (chemical formula below) was obtained as an oil. NMR (δ ppm in CDCl$_3$): 0.93 (3H, d, J=6 Hz), 0.94 (3H, d, J=6 Hz), 1.45–2.00 (7H, m), 2.50 (1H, broad), 3.61 (2H, t, J=6 Hz), 3.74 (3H, s), 4.14–4.30 (1H, m), 4.53–4.64 (1H, m), 5.10 (2H, s), 5.35 (1H, d, J=8.6 Hz), 7.03 (1H, d, J=8 Hz), 7.34 (5H, s). Optical rotation [α]$_D$−12.1° (c=0.58, CHCl$_3$)

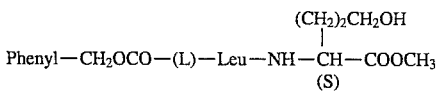

REFERENCE EXAMPLE 15

In substantially the same manner as Reference Example 13, (S)-3-[[N-benzyloxycarbonyl-(L)-leucyl]amino]-2-oxotetrahydropyran (chemical formula below) was synthesized. As recrystallized from dichloromethane-isopropyl ether, colorless crystals, m.p. 126°–127° C., optical rotation [α]$_D$+25.4° (C=0.50,

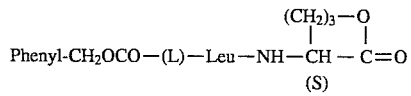

REFERENCE EXAMPLE 16 and 17

The compounds listed in Table 4 were synthesized in substantially the same manner as Reference Example 9.

TABLE 4

$$\text{R—NH—CH} \begin{array}{c} (CH_2)_2\text{—O} \\ | \quad\quad | \\ \text{— C=O} \end{array}$$
(S)

| Reference Example No. | R | Melting point (°C.) | Recrystallization solvent | Optical rotation [α]$_D$ (conc./solvent) |
|---|---|---|---|---|
| 16 | 1-Np—SO$_2$—(L)—Val— | 243–244 | Dichloromethane/methanol/isopropyl ether | −18.6° (c = 0.54, CHCl$_3$) |
| 17 | 1-Np—SO$_2$—(L)—Leu— | 186–188 | Chloroform/methanol/isopropyl ether | −78.6° (c = 0.28, CH$_3$OH) |

1-Np: 1-naphthyl, Val: valine, Leu: leucine

REFERENCE EXAMPLE 18 to 21

The compounds listed in Table 5 were synthesized in substantially the same manner as Reference Example 2.

TABLE 5

$$R-NH-CH-C=O \atop (S) \quad \overset{(CH_2)_2-O}{|\phantom{xx}|}$$

| Reference Example No. | R | Melting point (°C.) | Recrystallization solvent | Optical rotation $[\alpha]_D$ (conc./solvent) |
|---|---|---|---|---|
| 18 | Cbz—(L)—Leu— | 141–143 | Dichloromethane/isopropyl ether | −27.5° (c = 0.49, CHCl₃) |
| 19 | PhNHCO—(L)—Phe— | 198–200 | Methanol/isopropyl ether | +13.6° (c = 0.98, DMSO) |
| 20 | 1-Np—NHCO—(L)—Phe— | 235–237 | Chloroform/ether/ethanol | −3.1° (c = 0.595, DMSO) |
| 21 | (Ph)₂C=CH(CH₂)₄CO— | 96–98 | Ethyl acetate-hexane-ethanol | +10.7° (c = 0.50, CHCl₃) |

Cbz: benzyloxycarbonyl, 1-Np: 1-naphthyl, Ph: phenyl, Leu: leucine, Phe: phenylalanine, DMSO: dimethyl sulfoxide

REFERENCE EXAMPLE 22 to 26

The compounds listed in Table 6 were synthesized in substantially the same manner as Reference Example 8.

TABLE 6

$$R-NH-CH-C=O \atop (S) \quad \overset{(CH_2)_2-O}{|\phantom{xx}|}$$

| Reference Example No. | R | Melting point (°C.) | Recrystallization solvent | Optical rotation $[\alpha]_D$ (conc./solvent) |
|---|---|---|---|---|
| 22 | (PhCH₂)₂CHCO—(L)—Val— | 205–206 | Dichloromethane/methanol/isopropyl ether | −33.5° (c = 0.55, CHCl₃) |
| 23 | (C₃H₇)₂CHCO—(L)—Val— | 109–110 | Chloroform/methanol/hexane | −56.1° (c = 0.29, CHCl₃) |
| 24 | PhSCH₂CO—(L)—Phe— | 159–160 | Dichloromethane/isopropyl ether | −7.7° (c = 0.50, CHCl₃) |
| 25 | PhOCH₂CO—(L)—Phe— | 174–175 | N,N-Dimethylformamide/H₂O | −19.7° (c = 0.50, CHCl₃) |
| 26 | Cbz—(L)—Leu—(L)—Leu— | 192–194 | Dichloromethane/isopropyl ether | −64.7° (c = 0.53, CHCl₃) |

Ph: phenyl, Phe: phenylalanine, Leu: leucine, Val: valine, Cbz: benzyloxycarbonyl

REFERENCE EXAMPLE 27

In substantially the same manner as Reference Example 10, (S)-3-[[N-(1-naphthylthiocarbamoyl)-(L)-leucyl]amino]tetrahydrofuran-2-one (chemical formula below) was synthesized. As recrystallized from dichloromethane-isopropyl ether, colorless powder, m.p. 102°–105° C., optical rotation $[\alpha]_D$ −26.1° (C=0.47, CHCl₃).

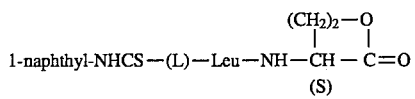

EXAMPLE 1

A solution of (S)-3-[[N-tert-butoxycarbonyl-(L)-phenylalanyl]amino]tetrahydrofuran-2-one (0.8 g) in tetrahydrofuran (THF) (30 ml) was prepared and a solution of diisobutylaluminum hydride (DIBAL-H) in toluene (1.5 M, 5.4 ml) was added dropwise to the above solution in an argon atmosphere at −72°–−69° C. The mixture was stirred at the same temperature for 30 minutes, after which a mixture of water and tetrahydrofuran (THF) (1:2, 3 ml) was added dropwise. This reaction mixture was diluted with ethyl acetate (300 ml) and stirred at room temperature for 1 hour. The insoluble matter was then filtered off and the filtrate was concentrated under reduced pressure. The residue was chromatographed on a silica gel column and elution was carried out with ethyl acetate-hexane (1:1, v/v). From the eluate was obtained (3S)-3-[[N-tert-butoxycarbonyl-(L)-phenylalanyl]amino]-2-hydroxytetrahydrofuran (chemical formula below) (0.3 g, 37.5%) as an amorphous solid.

m.p. 80°–90° C. NMR(δ ppm in CDCl₃): 1.41 (9H, S), 1.60–1.84 (1H, m), 1.93 (1H, d, J=5.6 Hz), 2.19–2.45 (1H, m), 2.94–3.15 (1H, m), 3.56–4.40 (5H, m), 5.00–5.23 (2H, m), 6.16–6.36 (1H, m), 7.18–7.39 (5H, m). Optical rotation $[\alpha]_D$ −10.1° (C=0.57, CHCl₃).

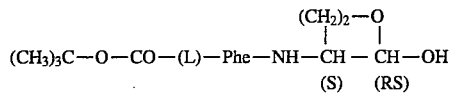

EXAMPLES 2–7

The compounds listed in Table 7 were synthesized by the same procedure as described in Example 1.

TABLE 7

$$R-NH-\underset{(S)}{CH}-\underset{(RS)}{\overset{\overset{(CH_2)_2-O}{|}}{CH}}-OH$$

| Example No. | R | Melting point (°C.) | Recrystallization solvent | Optical rotation $[\alpha]_D$ (conc./solvent) |
|---|---|---|---|---|
| 2 | $(PhCH_2)_2CHCO-$ | 125–126 | Dichloromethane/hexane | +25.5° (c = 0.5, $CHCl_3$) |
| 3 | $Cbz-(L)-Ile-$ | 165–167 | Chloroform/isopropyl ether | −15.6° (c = 0.49, $CHCl_3$) |
| 4 | $1-Np-SO_2-(L)-Ile-$ | 78–81[1] | Ethyl acetate/hexane/isopropyl ether | −8.5° (c = 0.5, $CHCl_3$) |
| 5 | $Cbz-(L)-Phe-$ | 144–146[2] | Dichloromethane/ether | −7.1° (c = 0.915, $CHCl_3$) |
| 6 | $Cbz-(L)-Val-$ | 154–155[3] | Ethyl acetate/hexane/isopropyl ether | −17.9° (c = 0.5, $CHCl_3$) |
| 7 | $(C_3H_7)_2CHCO-(L)-Phe-$ | 168–170 | Dichloromethane/ether | −23.6° (c = 0.5, $CHCl_3$) |

Ph: phenyl, Cbz: benzyloxycarbonyl, 1-Np: 1-naphthyl, Ile: isoleucine, Val: valine, Phe: phenylalanine
[1] Amorphous solid. [2] ¼ Hydrate. [3] ¼ Hydrate.
NMR (δ ppm in $CDCl_3$): 0.67–0.79 (6H, m), 0.90–1.10 (1H, m), 1.23–1.50 (2H, m), 1.60–1.85 (1H, m), 1.89–2.30 (1H, m), 2.78 (0.5H, d, J = 2 Hz), 2.99 (0.5H, d, J = 3 Hz), 3.39–3.51 (1H, m), 3.69–4.14 (3H, m), 4.96 (0.5H, d, J = 3 Hz), 5.10 (0.5H, t, J = 4 Hz), 5.43–5.51 (1H, m), 5.82 (0.5H, broad), 6.20 (0.5H, broad), 7.49–7.76 (3H, m), 7.92–7.97 (1H, m), 8.06–8.10 (1H, m), 8.63–8.68 (1H, m).

EXAMPLE 8

(3S)-3-[[N-tert-Butoxycarbonyl-(L)-phenylalanyl]amino]-2-hydroxytetrahydrofuran (0.1 g) was dissolved in acetic anhydride (3 ml) followed by addition of 4-dimethylaminopyridine (DMAP) (0,012 g) and the mixture was stirred at room temperature for 12 hours. The reaction mixture was then poured into water and extracted with ethyl acetate. The ethyl acetate layer was washed with 10% aqueous citric acid, water, saturated aqueous sodium hydrogen carbonate, and saturated aqueous sodium chloride in the order mentioned and dried ($MgSO_4$) and the solvent was distilled off to give (3S)-2-acetoxy-3-[[N-tert-butoxycarbonyl-(L)-phenylalanyl]amino]tetrahydrofuran (chemical formula below) (0,035 g, 29%). This product was recrystallized from ethyl acetate-hexane. Colorless crystals, m.p. 156°–157° C. Optical rotation $[\alpha]_D$−49.9° (C=0.15, $CHCl_3$).

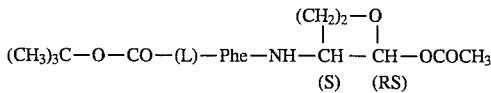

EXAMPLES 9–24

The compounds listed in Table 8 were synthesized in substantially the same manner as Example 1.

TABLE 8

$$R-NH-\underset{(S)}{CH}-\underset{(RS)}{\overset{\overset{(CH_2)_q-O}{|}}{CH}}-OH$$

| Example No. | R | q | Melting point (°C.) | Recrystallization solvent | Optical rotation $[\alpha]_D$ (conc./solvent) |
|---|---|---|---|---|---|
| 9 | $1-Np-SO_2-(L)-Phe-$ | 2 | 85–87 | Ethyl acetate/hexane | −74.6° (c = 0.50, $CHCl_3$) |
| 10 | $1-Np-SO_2-(L)-Val-$ | 2 | 158–161 | Isopropyl ether/hexane | −14.0° (c = 0.12, $CHCl_3$) |
| 11 | $(PhCH_2)_2CHCO-(L)-Val-$ | 2 | 83–86[1] | Isopropyl ether/hexane | −25.3° (c = 0.51, $CHCl_3$) |
| 12 | $(C_3H_7)_2CHCO-(L)-Val-$ | 2 | 189–191[2] | Isopropyl ether/hexane | −39.2° (c = 0.11, $CHCl_3$) |
| 13 | $PhSCH_2CO-(L)-Phe-$ | 2 | 140–142 | Dichloromethane/isopropyl ether | +1.9° (c = 0.50, $CHCl_3$) |
| 14 | $PhOCH_2CO-(L)-Phe-$ | 2 | 153–155 | | −1.9° (c = 0.50, $CHCl_3$) |
| 15 | $Cbz-(L)-Leu-$ | 2 | <40[3] | | −20.8° (c = 0.53, $CHCl_3$) |

TABLE 8-continued $$\begin{array}{c} (CH_2)_q-O \\ | \quad\quad\quad | \\ R-NH-CH-CH-OH \\ (S) \quad\quad (RS) \end{array}$$

| Example No. | R | q | Melting point (°C.) | Recrystallization solvent | Optical rotation $[\alpha]_D$ (conc./solvent) |
|---|---|---|---|---|---|
| 16 | Cbz—(L)—Leu—(L)—Leu— | 2 | 79–83[4)] | Isopropyl ether/hexane | −40.0° (c = 0.50, CHCl$_3$) |
| 17 | 1-Np—NHCO—(L)—Leu— | 2 | 191–192[5)] | Chloroform/methanol/isopropyl ether | +19.3° (c = 0.12, CHCl$_3$) |
| 18 | PhNHCO—(L)—Phe— | 2 | 158–160 | Methanol/ether | +24.9° (c = 0.755, DMSO) |
| 19 | 1-Np—NHCO—(L)—Phe— | 2 | 177–179 | Methanol/ether | +2.3° (c = 0.50, DMSO) |
| 20 | (Ph)$_2$C=CH(CH$_2$)$_4$—CO— | 2 | 90–92 | Ethyl acetate/hexane | −20.0° (c = 0.50, CHCl$_3$) |
| 21 | 1-Np—NHCS—(L)—Leu— | 2 | 102–105[6)] | Dichloromethane/isopropyl ether | −27.1° (c = 0.59, CHCl$_3$) |
| 22 | 1-Np—SO$_2$—(L)—Leu— | 2 | 78–85[7)] | Dichloromethane/isopropyl ether | −52.3° (c = 0.56, CHCl$_3$) |
| 23 | Cbz—(L)—Phe— | 3 | 173–174 | Dichloromethane/isopropyl ether/methanol | −14.8° (c = 0.51, CHCl$_3$) |
| 24 | Cbz—(L)—Leu— | 3 | 148–150 | Dichloromethane/isopropyl ether/methanol | −41.3° (c = 0.51, CHCl$_3$) |

[1)]¼ hydrate, [2)]¼ hydrate, [3)]¼ hydrate, [4)]¼ hydrate, [5)]¼ hydrate, [6)]⅓ isopropyl ether adduct, [7)]⅓ hydrate
Cbz: benzyloxycarbonyl, 1-Np: 1-naphthyl, Ph: phenyl, Phe: phenylalanine, Val: valine, Leu: leucine

EXAMPLE 25

In substantially the same manner as Example 8, (3S)-2-acetoxy-3-[[N-benzyloxycarbonyl-(L)-valyl]amino]tetrahydrofuran (chemical formula below) was obtained. As recrystallized from dichloromethaneisopropyl ether-hexane, colorless crystals, m.p. 173– 174° C., optical rotation $[\alpha]_D 59.0°$ (C=0.50, CHCl).

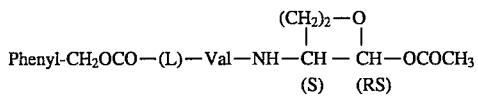

EXAMPLE 26

A solution of (S)-3-[[N-benzyloxycarbonyl-(L)-leucyl]amino]tetrahydrofuran-2-one (6.0 g) in tetrahydrofuran (250 ml) was prepared and a toluene solution of diisobutylaluminum hydride (1.5M, 51.6 ml) was added dropwise to the above solution in an argon atmosphere at −70°—−65° C. After the temperature was allowed to return to ambient temperature, the reaction mixture was diluted with ethyl acetate (400 ml) and, after addition of acetic anhydride (20 ml) and 4-dimethylaminopyridine (DMAP) (0.3 g), it was stirred at room temperature for 3 hours. This reaction mixture was then washed with 1N—HCl, water, saturated aqueous sodium hydrogen carbonate and saturated aqueous sodium chloride in the order mentioned and dried (MgSO$_4$) and the solvent was distilled off. The residue was chromatographed on a silica gel column and elution was carried out with ethyl acetate-hexane (1:1, v/v). From the eluate was obtained (2S,3S)-2-acetoxy-3-[[N-benzyloxycarbonyl-(L)-leucyl]amino]tetrahydrofuran (chemical formula below) (3.3 g, 49%). As recrystallized from dichloromethane-isopropyl ether, colorless needles, m.p. 161°–162° C., optical rotation $[\alpha]_D 86.6°$ (C=0.53, CHCl$_3$).

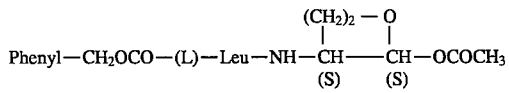

EXAMPLE 27

In substantially the same manner as Example 26, (3S)-2-acetoxy-3-[[N-benzyloxycarbonyl-(L)-leucyl]amino]tetrahydropyran (chemical formula below) was obtained. As recrystallized from dichloromethaneisopropyl ether, colorless crystals, m.p. 142°–143° C., optical rotation $[\alpha]_D -62.5°$ (c=0.50, CHCl$_3$).

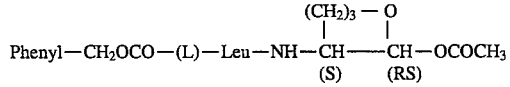

EXAMPLE 28

In substantially the same manner as Example 26, (2S,3S)-2-acetoxy-3-[[N-benzyloxycarbonyl-(L)-phenylalanyl]amino]tetrahydrofuran (chemical formula below) was obtained. As recrystallized from ethyl acetate, colorless needles, m.p. 175°–176° C., optical rotation $[\alpha]_D -61.4°$ (C=0.61, CHCl$_3$).

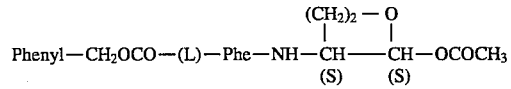

EXAMPLE 29

(2S, 3S)-2-Acetoxy-3-[[N-benzyloxycarbonyl-(L)leucyl]amino]tetrahydrofuran (3.2 g) was dissolved in ethanol (150 ml) followed by addition of palladium-on-carbon (5%, 1.5 g) and the catalytic hydrogenation was carried out at ambient temperature and atmospheric pressure. The catalyst was then filtered off and α-naphthyl isocyanate (1.5 g) was added to the filtrate. This mixture was stirred at room temperature for 3 hours. The reaction mixture was then concentrated under reduced pressure to obtain (2S,3S)-2-acetoxy-3-[[N-(1-naphthylcarbamoyl)-(L)-leucyl]amino]-tetrahydrofuran (chemical formula below) (2.95 g, 89%). As recrystallized from dichloromethane-methanol/isopropyl ether, colorless crystals, m.p. 196°–198° C., optical rotation $[\alpha]_D -51.8°$ (c=0.32, $CHCl_3$).

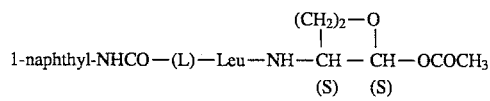

EXAMPLES 30 and 31

The compounds listed in Table 9 were synthesized in substantially the same manner as Example 29.

then filtered off and the filtrate was concentrated under reduced pressure. The oily residue was dissolved in N,N-dimethylformamide (DMF) (25 ml) and following addition of 1-naphthalenesulfonyl chloride (0.59 g), the mixture was cooled at 0° C. Then, 4-dimethylaminopyridine (DMAP) (0.32 g) was added and the mixture was stirred at 0° C. for 2 hours. The reaction mixture was then poured into water and extracted with ethyl acetate. The ethyl acetate layer was washed with 10% aqueous citric acid, water, saturated aqueous sodium hydrogen carbonate and saturated aqueous sodium chloride in the order mentioned and dried (($MgSO_4$)) and the solvent was distilled off, whereupon (3S)-2-acetoxy-3-[N-(1-naphthalenesulfonyl)-(L)-leucyl]amino]tetrahydropyran (chemical formula below) (0.83 g, 69%) was obtained. As recrystallized from dichloromethane-methanol-isopropyl ether, colorless prisms, m.p. 180°–182° C., optical rotation $[\alpha]_D -154.5°$ (C=0.51, $CHCl_3$).

Elemental analysis for $C_{23}H_{30}N_2O_6S \cdot 1/2\ H_2O$ Calcd.: C, 58.58; H, 6.63; N, 5.94 Found : C, 58.69; H, 6.33; N, 5.92

TABLE 9

$$R-NH-CH(\overset{(S)}{\underset{|}{}})-CH(\overset{(RS)}{\underset{|}{}})-OCOCH_3 \quad \text{with } (CH_2)_3-O \text{ ring}$$

| Example No. | R | Melting point (°C.) | Recrystallization solvent | Optical rotation $[\alpha]_D$ (conc./solvent) |
|---|---|---|---|---|
| 30 | 1-Np—NHCO—(L)—Phe— | 209–212 | Dichloromethane/methanol/isopropyl ether | −34.7° (c = 0.50, $CHCl_3$) |
| 31 | 1-Np—NHCO—(L)—Leu— | 198–202 | Dichloromethane/methanol/isopropyl ether | −26.1° (c = 0.33, $CHCl_3$) |

1-Np: 1-naphthyl, Phe: phenylalanine, Leu: Leucine

EXAMPLE 32

(2S,3S)-2-Acetoxy-3-[[N-(1-naphthylcarbamoyl)-(L)-leucyl]amino]tetrahydrofuran (2.9 g) was suspended in methanol (50 ml) followed by addition of a solution of potassium carbonate (0.94 g) in water (5 ml) under ice-cooling and the mixture was stirred at room temperature for 1 hour. The reaction mixture was then poured into water and extracted with ethyl acetate. The ethyl acetate layer was washed with water and dried ($MgSO_4$) and the solvent was distilled off to give 2-hydroxy-3-[[N-(1-naphthylcarbamoyl)-(L)-leucyl]amino]tetrahydrofuran (chemical formula below) (1.95 g, 72%). As recrystallized from dichloromethane-methanol/isopropyl ether, colorless crystals, m.p. 177°–178° C., optical rotation $[\alpha]_D +29.5°$ (c=0.25, dimethyl sulfoxide).

Elemental analysis for $C_{21}H_{27}N_3O_4 \cdot 1/2\ H_2O$ Calcd.: C, 63.94; H, 7.15; N, 10.65 Found : C, 64.62; H, 7.09; N, 10.78

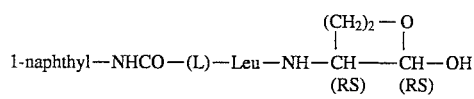

EXAMPLE 33

(3S)-2-Acetoxy-3-[[N-benzyloxycarbonyl-(L)-leucyl] amino]tetrahydropyran (1.0 g) was dissolved in ethanol (100 ml) followed by addition of palladium-on-carbon (5%, 0.3 g) and the catalytic hydrogenation was carried out at ambient temperature and atmospheric pressure. The catalyst was

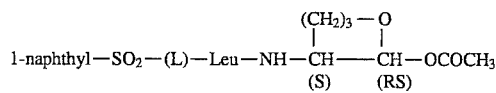

EXAMPLE 34

In substantially the same manner as Example 33, (2S,3S)-2-acetoxy-3-[[N-(4-nitrobenzenesulfonyl)-(L)-leucyl] amino]tetrahydrofuran (chemical formula below) was synthesized. As recrystallized from ethyl acetate-methanol, colorless needles, m.p. 197°–199° C., optical rotation $[\alpha]_D -81.4°$ (C=0.45, $CHCl_3$).

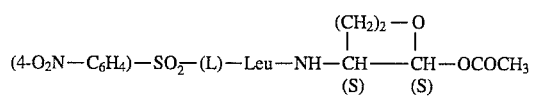

EXAMPLE 35

In tetrahydrofuran (20 ml ) was suspended (3S )-2-acetoxy-3-[N-(1-naphthalenesulfonyl )-(L )-leucyl ]amino ]-tetrahydropyran (0.5 g) and following addition of 1N—HCl (5 ml), the mixture was stirred at room temperature for 65 hours. The reaction mixture was then poured into water and extracted with ethyl acetate. The ethyl acetate layer was washed with water, dried (($MgSO_4$)) and the solvent was distilled off. The residue was chromatographed on a silica gel column and eluted with ethyl acetate-hexane (1:1, v/v). From the eluate was obtained (3S)-2-hydroxy-3-[[N-(1-naphthalenesulfonyl)-(L)-leucyl]amino]tetrahydropyran (chemical formula below) (0.31 g, 69%). As recrystallized from dichloromethane-isopropyl ether, colorless crystals, m.p. 159°–161° C., optical rotation $[\alpha]_D$ –81.5° (C=0.27, CHCl₃).

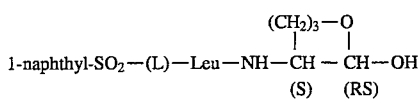

1-naphthyl-SO₂—(L)—Leu—NH—CH—CH—OH
                                   (S)   (RS)

EXAMPLES 36–53

The compounds listed in Table 10 were synthesized in substantially the same manner as Example 35.

TABLE 10

$$\begin{array}{c} (CH_2)_q-O \\ | \quad\quad | \\ R-NH-CH-CH-OH \\ (S) \quad\quad (RS) \end{array}$$

| Example No. | R | q | Melting point (°C.) | Recrystallization solvent | Optical rotation $[\alpha]_D$ (conc./solvent) |
|---|---|---|---|---|---|
| 36 | 1-Np—NHCO—(L)—Leu— | 3 | 205–206 | Dichloromethane/methanol | +10.2° (c = 0.27, dimethyl sulfoxide) |
| 37 | CH₃CO—(L)—Leu—(L)—Leu | 2 | 108–112[1] | Dichloromethane/isopropyl ether | –92.0° (c = 0.25, CHCl₃) |
| 38 | Cbz—(L)—Leu—(L)—Leu— | 3 | 180–182 | Dichloromethane/methanol/isopropyl ether | –64.1° (c = 0.27, CHCl₃) |
| 39 | CH₃CO—(L)—Leu—(L)—Leu— | 3 | 216–217 | Dichloromethane/methanol/ethyl acetate | –61.1° (c = 0.26, DMSO) |
| 40 | T—(L)—Leu— | 2 | 89–90[3] | | –36.6° (c = 0.50, CHCl₃) |
| 41 | (C₃H₇)₂CHCO—(L)—Leu— | 2 | 150–156[4] | | –65.0° (c = 0.54, CHCl₃) |
| 42 | S—(L)—Leu— | 2 | 65–75[5] | | –5.2° (c = 0.54, CHCl₃) |
| 43 | U—(L)—Leu— | 2 | 171–173 | Dichloromethane/methanol/ethyl acetate | –32.1° (c = 0.51, dimethyl sulfoxide |
| 44 | quinolyl—CO—(L)—Leu— | 2 | 90–92[7] | Dichloromethane/isopropyl ether | +24.7° (c = 0.55, CHCl₃) |
| 45 | nicotinoyl—(L)—Leu— | 2 | 158–160[8] | Dichloromethane/methanol/isopropyl ether | +35.6° (c = 0.30, DMSO) |
| 46 | V—(L)—Leu— | 2 | 125–135[9] | Ethyl acetate/methanol/isopropyl ether | –21.9° (c = 0.30, DMSO) |
| 47 | 2-pyridyl—CO—(L)—Leu— | 2 | 63–68[10] | | –31.0° (c = 0.56, CHCl₃) |
| 48 | 4-pyridyl—CO—(L)—Leu— | 2 | 109–114 | Ethyl acetate/hexane | –16.6° (c = 0.32, CHCl₃) |
| 49 | Q—(L)—Leu— | 2 | 124–125[11] | Ethyl acetate/hexane | +1.3° (c = 0.52, CHCl₃) |
| 50 | P—(L)—Leu— | 2 | 106–111[12] | Dichloromethane/isopropyl ether | –1.6° (c = 0.31, CHCl₃) |
| 51 | D—(L)—Leu— | 2 | 217–219[13] | Dichloromethane/isopropyl ether | +96.9° (c = 0.25, DMSO) |
| 52 | E—(L)—Leu— | 2 | 176–178 | Ethyl acetate/hexane | +10.8° (c = 0.25, DMSO) |
| 53 | quinolyl—CO—(L)—Val— | 2 | 80–85[14] | | +81.8° (c = 0.50, CHCl₃) |

[1] ⅓ isopropyl ether adduct, [3] amorphous solid, ½ hydrate, [4] amorphous solid, ¼ hydrate, [5] amorphous solid, ½ hydrate, [7] ¼ [(CH₃)₂CH]₂O adduct, elemental analysis: calcd. for C₂₀H₂₅N₃O₄·¼[CH₃)₂CH]₂O: C, 65.05; H, 7.24; N, 10.58; found C, 65.30; H, 7.62; H, 10.22, [8] ¼ hydrate, elemental analysis: calcd. for C₁₆H₂₃N₃O₄·⅓[CH ₃)₂CH]₂O·¼H₂O: C, 59.65; H, 7.65; N, 12.15; found C, 59.70; H, 7.63; H, 11.94, [9] elemental analysis: calcd. for C₂₃H₃₀N₂O₇·⅓[CH₃)₂CH]₂O·¼H₂O: C, 59.65; H, 7.65; N, 12.15; found C, 59.70; H, 7.63; H, 11.94, [10] amorphous solid, ½ hydrate, [11] ¼ hydrate, [12] elemental analysis: calcd. for C₂₃ H₃₀N₂O₇·¼[(CH₃)₂CH]₂)O·¼H₂O: C, 63.71; H, 7.06; N, 8.41; found C, 63.55; H, 7.09; N, 8.23, [13] elemental analysis: calcd. for C₁₇H₂₅N₃O₄·⅓[(CH₃)₂CH]₂O·¼H₂O: C, 60.45; H, 7.51; N, 12.53; found C, 60.69; H, 7.45; H, 11.86, [14] amorphous solid, ¼ hydrate 1-Np: 1-naphthyl, Phe: phenylalanine, Leu: leucine, Val: valine, DMSO: dimenthyl sulfoxide, T: 6-hydroxy-2,5,7,8-tetramethyl-chroman-2-ylcarbonyl, S: 4-diethoxyphosphorylmethylbenzoyl, U: 2-phenyl-5-methyl-4-oxazolylacetyl, V: 2,3-methylenedioxy-6,7,8,9-tetrahydro-5-oxo-5H-benzocycloheptene-8-carbonyl, Q: 4-methoxycarbonylbenzoyl, E: 4-nitrobenzenesulfonyl, P: 4-(N-benzyloxycarbonylamino)benzoyl, D: 4-aminobenzoyl

EXAMPLE 54

In ethanol (100 ml) was dissolved (2S,3S)-2-acetoxy-3-[[N-benzyloxycarbonyl-(L)-leucyl]amino]tetrahydrofuran (1.5 g) and following addition of palladium-on-carbon (5%, 0.5 g), the catalytic hydrogenation was carried out at ambient temperature and atmospheric pressure. The catalyst was filtered off and the filtrate was concentrated under reduced pressure. The oily residue was dissolved in N,N-dimethylformamide (DMF) (20 ml) followed by addition of N-benzyloxycarbonyl-(L)-leucine (Cbz-Leu-OH) (1.1 g) and 1-hydroxybenzotriazole (HOBt) (0.64 g). This mixture was cooled to 0° C. and 1-ethyl-3-(3-dimethylaminopropyl)carbodiimide hydrochloride (WSCD.HCl) (0.88 g) was added. The mixture was stirred at 0° C. for 1 hour and then at room temperature for 15 hours. This reaction mixture was poured into ice-water and extracted with ethyl acetate. The ethyl acetate layer was washed with 10% aqueous citric acid, water, saturated aqueous sodium hydrogen carbonate and saturated aqueous sodium chloride in the order mentioned and dried (MgSO$_4$) and the solvent was distilled off, whereby (2S,3S)-2-acetoxy-3-[[N-benzyloxycarbonyl-(L)-leucyl-(L)-leucyl]amino]tetrahydrofuran (chemical formula below) (1.6 g, 84%) was obtained. As recrystallized from dichloromethane-isopropyl ether, colorless crystals, m.p. 175°–176° C., optical rotation [α]$_D$–104.3° (C=0.52, CHCl$_3$).

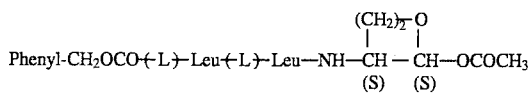

EXAMPLES 55–69

The compounds listed in Table 11 were synthesized in substantially the same manner as Example 54.
[Table 11 ]

concentrated under reduced pressure. The oily residue was dissolved in dichloromethane (20 ml) and following addition of acetic anhydride (0.3 g) and 4-dimethylaminopyridine (DMAP) (0.061 g), and the mixture was stirred at room temperature for 15 hours. This reaction mixture was poured into ice-water and extracted with ethyl acetate. The ethyl acetate layer was washed with 10% aqueous citric acid, water, saturated aqueous sodium hydrogen carbonate and saturated aqueous sodium chloride in the order mentioned and dried ((MgSO$_4$) and the solvent was distilled off, whereupon (2S,3S)-2-acetoxy-3-[[N-acetyl-(L)-leucyl-(L)-leucyl]amino]tetrahydrofuran (chemical structure below) (0.43 g, 74%) was obtained. As recrystallized from dichloromethane-isopropyl ether, colorless crystals, m.p. 210°–211° C., optical rotation [α]$_D$–147.8° (C=0.27, CHCl$_3$).

$$\begin{array}{c} \phantom{R-NH-CH-}(CH_2)_q-O \\ \phantom{R-NH-CH-}|\phantom{xxxx}| \\ R-NH-CH\ -\ CH-OCOCH_3 \\ \phantom{R-NH-}(S)\phantom{xx}(S) \end{array}$$

| Example No. | R | q | Melting point (°C.) | Recrystallization solvent | Optical rotation [α]$_D$ (conc./solvent) |
|---|---|---|---|---|---|
| 55 | Cbz—(L)—Leu—(L)—Leu— | 3 | 168–170[1)] | Dichloromethane/isopropyl ether | −79.3° (c = 0.27, CHCl$_3$) |
| 56 | T—(L)—Leu— | 2 | 75–80[2)] |  | −89.5° (c = 0.50, CHCl$_3$) |
| 57 | (C$_3$H$_7$)$_2$CHCO—(L)—Leu— | 2 | 223–224 | Ethyl acetate/hexane | −132.2° (c = 0.50, CHCl$_3$) |
| 58 | S—(L)—Leu— | 2 | 69–75[3)] |  | −54.0° (c = 0.51, CHCl$_3$) |
| 59 | U—(L)—Leu— | 2 | 186–188 | Dichloromethane/isopropyl ether | −93.6° (c = 0.26, CHCl$_3$) |
| 60 | (C$_3$H$_7$)$_2$CHCO—(L)—Val— | 2 | 175–176 | Ethyl acetate/methanol | −109.5° (c = 0.49, CHCl$_3$) |
| 61 | quinolyl—CO—(L)—Leu— | 2 | 150–151 | Dichloromethane/isopropyl ether | −36.0° (c = 0.55, CHCl$_3$) |
| 62 | nicotinoyl—(L)—Leu— | 2 | 168–170 | Dichloromethane/isopropyl ether | −78.7° (c = 0.51, CHCl$_3$) |
| 63 | V—(L)—Leu— | 2 | 217–222 | Ethyl acetate/methanol | −71.0° (c = 0.52, CHCl$_3$) |
| 64 | 2-pyridyl—CO—(L)—Leu— | 2 | 45–50[4)] |  | −97.6° (c = 0.53, CHCl$_3$) |
| 65 | 4-pyridyl—CO—(L)—Leu— | 2 | 189–190 | Dichloromethane/isopropyl ether | −85.2° (c = 0.50, CHCl$_3$) |
| 66 | Q—(L)—Leu— | 2 | 214–215 | Ethyl acetate/methanol | −63.4° (c = 0.27, CHCl$_3$) |
| 67 | P—(L)—Leu— | 2 | 206–207 | Chloroform/methanol/isopropyl ether | −13.8° (c = 0.29, DMSO) |
| 68 | quinolyl—CO—(L)—Val— | 2 | 156–158 | Dichloromethane/isopropyl ether | −2.7° (c = 0.53, CHCl$_3$) |
| 69 | PhOCH$_2$CO—(L)—Phe— | 2 | 156–157 | Ethyl acetate | −64.3° (c = 0.52, CHCl$_3$) |

[1)](2RS)-compound, [2)]amorphous solid, [3)]amorphous solid, ¼ hydrate, [4)]amorphous solid, monohydrate, Cbz: benzyloxycarbonyl, Leu: leucine, Val: valine, Phe: phenylalanine, DMSO: dimethyl sulfoxide, T: 6-hydroxy-2,5,7,8-tetramethyl-chroman-2-ylcarbonyl, S: 4-diethoxyphosphorylmethylbenzoyl, U: 2-phenyl-5-methyl-4-oxazolylacetyl, V: 2,3-methylenedioxy-6,7,8,9-tetrahydro-5-oxo-5H-benzocycloheptene-8-carbonyl, Q: 4-methoxycarbonylbenzoyl, P: 4-(N -benzyloxycarbonylamino)benzoyl

EXAMPLE 70

In ethanol (100 ml) was dissolved (2S,3S)-2-acetoxy-3-[[N-benzyloxycarbonyl-(L)-leucyl-(L)-leucyl]amino]tetrahydrofuran (0.7 g) followed by addition of palladium-on-carbon (5%, 0.25 g) and the catalytic hydrogenation was carried out at ambient temperature and atmospheric pressure. The catalyst was filtered off and the filtrate was

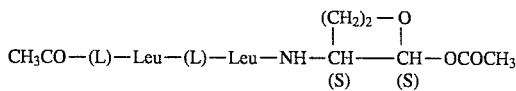

EXAMPLE 71

The procedure of Example 70 was substantially followed to give (3S)-2-acetoxy-3-[[N-acetyl-(L)-leucyl-(L)-leucyl]amino]tetrahydropyran (chemical structure below).

As recrystallized from dichloromethane-methanol, colorless crystals, m.p. 238°–240° C., optical rotation [α]$_D$– 112.1° (C=0.27, CHCl$_3$).

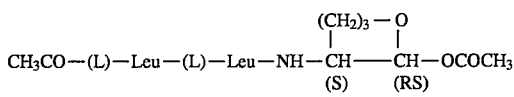

EXAMPLE 72

A solution of (S)-3-(N-benzyloxycarbonylamino)tetrahydrofuran-2-one (4.9 g) in tetrahydrofuran (150 ml) was prepared and a toluene solution of diisobutylaluminum hydride (1.5M, 28.0 ml) was added dropwise to the above solution in an argon atmosphere at −70°—65° C. Then, water (5 ml) was added dropwise at the same temperature followed by addition of acetic anhydride (20 ml) and 4-dimethylaminopyridine (DMAP) (0.3 g). After the temperature had risen to room temperature, the reaction mixture was diluted with ethyl acetate (400 ml) and the dilution was stirred at room temperature for 3 hours. The reaction mixture was washed with 1N—HCl, water, saturated aqueous sodium hydrogen carbonate and saturated aqueous sodium chloride in the order mentioned and dried (MgSO$_4$) and the solvent was distilled off. The residue was chromatographed on a silica gel column and elution was carried out with ethyl acetate-hexane (1:1, v/v). From the eluate was obtained (3S)-2-acetoxy-3-(N-benzyloxycarbonylamino)tetrahydrofuran as an oil. This oil was suspended in methanol (50 ml) followed by addition of concentrated hydrochloric acid (5 drops) and the mixture was stirred at room temperature for 1 hour. This reaction mixture was concentrated under reduced pressure to give (3S)-3-(N-benzyloxycarbonylamino)-2-methoxytetrahydrofuran as an oil (2.3 g, 44%). NMR δ ppm in CDCl$_3$): 1.64–1.80 (1H, m), 2.28–2.48 (1H, m), 3.32 (3H, s), 3.84–4.08 (2H, m), 4.10–4.20 (1H, m), 4.80 (1H, s), 4.80 (1H, broad), 5.10 (2H, s), 7.35 (5H, s).

EXAMPLE 73

In methanol (50 ml) was suspended (2S, 3S)-2-acetoxy-3-[[N-valproyl-(L)-valyl]amino]tetrahydrofuran (0.55 g) followed by addition of concentrated hydrochloric acid (5 drops) and the mixture was stirred at room temperature for 1 hour. The reaction mixture was then concentrated under reduced pressure to obtain (2S,3S)-2-methoxy-3-[[N-valproyl-(L)-valyl]amino]tetrahydrofuran (chemical structure below) (0.38 g, 72%). As recrystallized from ethyl acetate, colorless crystals, m.p. 150°–156° C., optical rotation [α]$_{D+}$ 18.5° (c=0.50, CHCl$_3$).

Elemental analysis for C$_{18}$H$_{34}$N$_2$O$_4$.1/4 H$_2$O Calcd: C, 62.31; H, 10.02; N, 8.07 Found: C, 62.33; H, 9.69; N, 8.10

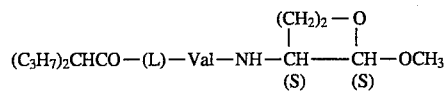

EXAMPLE 74

In tetrahydrofuran (100 ml )-methanol (40 ml ) was dissolved (3S)-3-(N-benzyloxycarbonylamino)-2-methoxytetrahydrofuran (2.3 g) and following addition of palladium-on-carbon (5%, 0.5 g), the catalytic hydrogenation was carried out at ambient temperature and atmospheric pressure. The catalyst was then filtered off and the filtrate was concentrated under reduced pressure. The oily residue was dissolved in N,N-dimethylformamide (DMF) (20 ml) followed by addition of N-benzyloxycarbonyl-(L)-aspartic acid β-methyl ester [Cbz-Asp(OCH$_3$)-OH] (2.8 g) and 1-hydroxybenzotriazole (HOBt) (1.5 g). This mixture was cooled to 0° C. and 1-ethyl-3-(3-dimethylaminopropyl)carbodiimide hydrochloride (WSCD.HCl) (2.1 g) was added. The mixture was stirred at 0° C. for 1 hour and, then, at room temperature for 15 hours. The reaction mixture was then poured into ice-water and extracted with ethyl acetate. The ethyl acetate layer was washed with 10% aqueous citric acid, water, saturated aqueous sodium hydrogen carbonate and saturated aqueous sodium chloride and dried (MgSO$_4$) and the solvent was distilled off, whereupon (3S)-3-[[N-benzyloxycarbonyl-(L)-(3-methoxycarbonyl)alanyl]amino]-2-methoxytetrahydrofuran (chemical formula below) (0.95 g, 48%) was obtained. As recrystallized from ethyl acetate-hexane, colorless crystals, m.p. 175°–176° C., optical rotation [α]D+43.7° (C=0.50, CHCl$_3$).

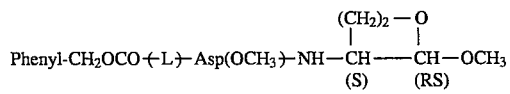

EXAMPLES 75–79

The compounds listed in Table 12 were synthesized in substantially the same manner as Example 74.

[Table 12]

| | (CH$_2$)$_2$—O | |
| | R—NH—CH — CH—OCH$_3$ | |
| | (S)   (RS) | |

| Example No. | R | Melting point (°C.) | Recrystallization solvent | Optical rotation [α]$_D$ (conc./solvent) |
|---|---|---|---|---|
| 75 | Cbz—(L)—Ala— | 143–144 | Ethyl acetate | +4.4° (c = 0.48, CHCl$_3$) |
| 76 | Cbz—Gly— | Oil[1)] | | +1.1° (c = 0.50, CHCl$_3$) |
| 77 | Cbz—(L)—Met— | 103–104 | Ethyl acetate/hexane | +11.3° (c = 0.51, CHCl$_3$) |
| 78 | Cbz—(L)—Tyr— | 127–129 | Ethyl acetate/hexane | −21.1° (c = 0.17, CHCl$_3$) |

-continued

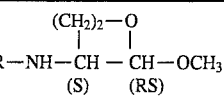

| Example No. | R | Melting point (°C.) | Recrystallization solvent | Optical rotation $[\alpha]_D$ (conc./solvent) |
|---|---|---|---|---|
| 79 | Cbz—(L)—Ile— | 164–166 | Ethyl acetate | +3.0° (c = 0.20, CHCl$_3$) |

[1])NMR (δ ppm in CDCl$_3$): 1.60–1.80 (1H, m), 2.20–2.45 (1H, m), 3.30 & 3.35 (3H, each s), 3.82–4.10 (4H, m), 4.30–4.50 (1H, m), 4.76–4.80 (1H, m), 5.11 & 5.13 (2H, each s), 5.62 (1H, broad), 6.44 (1H, broad), 7.34 (5H, s).
Cbz: benzyloxycarbonyl, Ala: alanine, Gly: glycine, Tyr: tyrosine, Met: methionine; Ile: isoleucine

EXAMPLE 80

In tetrahydrofuran (20 ml) was suspended (3S)- 3-[[N-benzyloxycarbonyl-(L)-(3-methoxycarbonyl)alanyl]amino]-2-methoxytetrahydrofuran (0.6 g) followed by addition of 1N—HCl (5 ml) and the mixture was stirred at room temperature for 72 hours. The reaction mixture was then poured into a saturated aqueous solution of sodium hydrogen carbonate and extracted with ethyl acetate. The ethyl acetate layer was washed with water, dried ((MgSO$_4$) and the solvent was distilled off. The residue was chromatographed on a silica gel column and elution was carried out with ethyl acetate-hexane (2:1, v/v). From the eluate was obtained (3S)-3-[[N-benzyloxycarbonyl-(L)-(3methoxycarbonyl)alanyl]amino]-2-hydroxytetrahydrofuran (chemical structure below) (0.06 g, 10%). As recrystallized from ethyl acetate, colorless prisms, m.p. 143°–145° C., optical rotation $[\alpha]_D$+14.6° (C=0.27, CHCl$_3$).

$$\text{Phenyl-CH}_2\text{OCO—(L)—Asp(OCH}_3\text{)—NH—CH—CH—OH} \quad \underset{(S)}{\phantom{x}} \underset{(RS)}{\phantom{x}}$$
with (CH$_2$)$_2$—O bridge

EXAMPLES 81–84

The procedure of Example 80 was substantially followed to give the compounds listed in Table 13.
[Table 13]

EXAMPLE 85

In tetrahydrofuran (10 ml) was suspended (2S,3S)-2-acetoxy-3-[[N-benzyloxycarbonyl-(L)-leucyl]amino]tetrahydrofuran (0.8 g) and following addition of p-toluenesulfonic acid (0.02 g) and ethyl glycolate (5 ml), the mixture was stirred at room temperature for 5 hours. The reaction mixture was then concentrated under reduced pressure and the residue was chromatographed on a silica gel column, elution being carried out with ethyl acetate-hexane (1:1, v/v). From the eluate was obtained ethyl [(3S)-3-[[N-benzyloxycarbonyl-(L)-leucyl]amino]tetrahydrofuran-2-yl]oxyacetate (0.6 g) as an oil. This oil was dissolved in methanol (5 ml) followed by addition of potassium carbonate (0.1 g)-water (5 ml) and the mixture was stirred at room temperature for 3 hours. This reaction mixture was neutralized with 1N—HCl and extracted with ethyl acetate. The ethyl acetate layer was washed with water and dried ((MgSO$_4$) and the solvent was distilled off. The residue was dissolved in ethanol (20 ml) and following addition of 1N—NaOH (0.6 ml), the mixture was stirred at room temperature for 30 minutes. The reaction mixture was then concentrated under reduced pressure to provide sodium [(3S)-3-[[N-benzyloxycarbonyl-(L)-leucyl]amino]tetrahydrofuran-2-yl]oxyacetate (chemical formula below) (0.35 g, 41%). As recrystallized from methanol-ether, colorless powder, m.p. 125°–127° C., optical rotation $[\alpha]_D$+50.7° (c=0.33, dimethyl sulfoxide)

Elemental analysis for C$_{20}$H$_{27}$N$_2$O$_7$Na.1/2 H$_2$O Calcd.: C, 54.66; H, 6.42; N, 6.37 Found : C, 54.30; H, 6.52; N, 6.27

TABLE 13

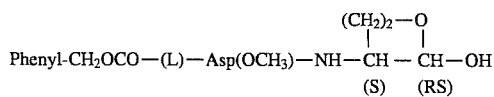

| Example No. | R | Melting point (°C.) | Recrystallization solvent | Optical rotation $[\alpha]_D$ (conc./solvent) |
|---|---|---|---|---|
| 81 | Cbz—(L)—Ala— | 165–167 | Ethyl acetate/methanol | −26.1° (c = 0.23, CHCl$_3$) |
| 82 | Cbz—Gly— | 130–131 | Ethyl acetate | −15.9° (c = 0.49, CHCl$_3$) |
| 83 | Cbz—(L)—Met— | 166–167 | Ethyl acetate/methanol | −20.1° (c = 0.49, DMSO) |
| 84 | Cbz—(L)—Tyr— | 163–165 | Dichloromethane/methanol/isopropyl ether | −16.0° (c = 0.17, DMSO) |

Cbz: benzyloxycarbonyl, Ala: alanine, Gly: glycine, Met: methionine; Tyr: tyrosine, DMSO: dimethyl sulfoxide

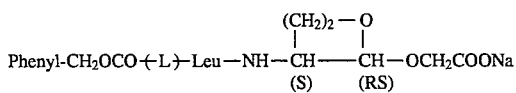

EXAMPLE 86

In ethanol (100 ml) was dissolved (2S,3S)-2-acetoxy-3-[[N-[4-(N-benzyloxycarbonylamino)benzoyl]-(L)-leucyl]amino]tetrahydrofuran (1.0 g) and following addition of palladium-on-carbon (5%, 0.7 g), the catalytic hydrogenation was carried out at ambient temperature and atmospheric pressure. The catalyst was then filtered off and the filtrate was concentrated under reduced pressure to provide (2S, 3S)-2-acetoxy-3-[[N-(4-aminobenzoyl)-(L)-leucyl]amino]tetrahydrofuran (chemical formula below) (0.61 g, 81%). As recrystallied from dichloromethane-isopropyl ether, colorless crystals, m.p. 148°–150° C. optical rotation $[\alpha]_D$–61.3° (C=0.29, CHCl$_3$).

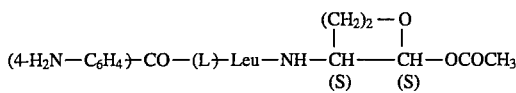

EXAMPLE 87

In ethanol (100 ml) was dissolved (2S,3S)-2-acetoxy-3-[[N-(4-nitrobenzenesulfonyl)-(L)-leucyl]amino]tetrahydrofuran (1.0 g) followed by addition of palladum-on-carbon (5%, 0.5 g) and the catalytic hydrogenation was carried out at ambient temperature and atmospheric pressure. The catalyst was filtered off and the filtrate was concentrated under reduced pressure to provide (2S,3S)-2-acetoxy-3-[[N-(4-aminobenzenesulfonyl)-(L)-leucyl]amino]tetrahydrofuran (chemical formula below) (0.7 g, 74%). As recrystallized from ethyl acetate-methonol-ether, colorless needles, m.p. 189°–190° C., optical rotation $[\alpha]_D$–59.2° (C=0.27, dimethyl sulfoxide)

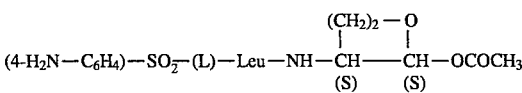

EXAMPLE 88

In methanol (250 ml) was dissolved (3S)-3-[[N-benzyloxycarbonyl-(L)-isoleucyl]amino]-2-methoxytetrahydrofuran (8.5 g) and following addition of palladum-on-carbon (5%, 2.3 g), the catalytic hydrogenation was carried out at ambient temperature and atmospheric pressure. The catalyst was then filtered off and the filtrate was concentrated under reduced pressure. The oily residue was dissolved in N,N-dimethylformamide (DMF) (50 ml) followed by addition of 1-naphthalenesulfonyl chloride (5.6 g) and 4-dimethylaminopyridine (DMAP) (3.0 g) and the mixture was stirred at 0° C. for 4 hours. The reaction mixture was then poured into ice-water and extracted with ethyl acetate. The ethyl acetate layer was washed with 10% aqueous citric acid, water, saturated aqueous sodium hydrogen carbonate and saturated aqueous sodium chloride in the order mentioned, dried (MgSO$_4$) and the solvent was distilled off to provide (3S)-2-methoxy-3-[[N-(1-naphthalenesulfonyl)-(L)-isoleucyl]amino]tetrahydrofuran (chemical formula below) (7.0 g, 71%). As recrystallized from ethyl acetate-hexane, colorless crystals, m.p. 125°–127° C., optical rotation $[\alpha]_D$+12.8° (C=0.56, CHCl$_3$).

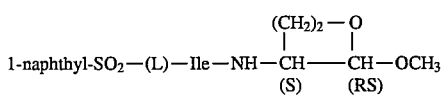

EXAMPLE 89

In methanol (20 ml) was suspended (2S,3S)-2-acetoxy-3-[[N-(1-naphthylcarbamoyl)-(L)-leucyl]amino]tetrahydrofuran (0.1 g) and following addition of concentrated hydrochloric acid (5 drops), the mixture was stirred at room temperature for 1 hour. The reaction mixture was then concentrated under reduced pressure to give (3S)-2-methoxy-3-[[N-(1-naphthylcarbamoyl)-(L)-leucyl]amino]-tetrahydrofuran (chemical structure below) (0.08 g, 87%). As recrystallized from dichloromethane-isopropyl ether, colorless crystals, m.p. 184°–185° C., optical rotation $[\alpha]_D$+13.0° (C=0.27, CHCl$_3$).

Elemental analysis for $C_{22}H_{29}N_3O_4 \cdot 1/4 \ H_2O$ Calcd.: C, 65.41; H, 7.36; N, 10.40 Found : C, 65.42; H, 7.52; N, 10.39

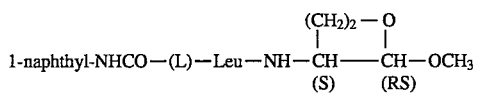

EXAMPLE 90

In substantially the same manner as Example 26, (3S)-2-acetoxy-3-[[N-benzyloxycarbonyl-(L)-isoleucyl]amino]tetrahydrofuran (chemical formula below) was synthesized. As recrystallized from ethyl acetate-hexane, colorless needles, m.p. 185°–187° C., optical rotation $[\alpha]_D$–68.1° (C=0.53, CHCl$_3$).

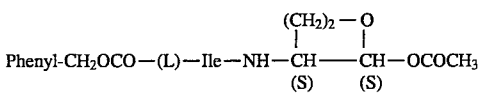

EXAMPLE 91

In substantially the same manner as Example 33, (2S, 3S)-2-acetoxy-3-[[N-(1-naphthalenesulfonyl)-(L)-isoleucyl]amino]tetrahydrofuran (chemical formula below) was synthesized. As recrystallized from dichloromethane-isopropyl ether, colorless needles, m.p. 158°–160° C., optical rotation $[\alpha]_D$–153.0° (C=0.50, CHCl$_3$).

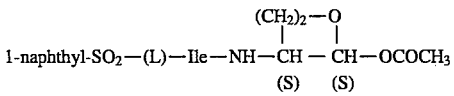

EXAMPLE 92

In substantially the same manner as Example 26, (2S,3S)-2-acetoxy-3-[[N-benzyloxycarbonyl-(L)-valyl]amino]tetrahydrofuran (chemical formula below) was synthesized. As recrystallized from ethyl acetate, colorless crystals, m.p. 161°–162° C., optical rotation $[\alpha]_D$66.6° (c=0.53, CHCl$_3$).

Elemental analysis for $C_{19}H_{26}N_2O_6 \cdot 1/4 \ H_2O$ Calcd.: C, 59.60; H, 6.98; N, 7.32 Found : C, 59.82; H, 6.77; N, 7.19

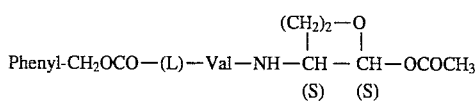

EXAMPLES 93–98

The compounds listed in Table 14 were synthesized in substantially the same manner as Example 35.

[Table 14]

EXAMPLE 107

In substantially the same manner as Example 8, (2S,3S)-3-[[N-(1-naphthalenesulfonyl)-(L)-isoleucyl]amino]-2-propionyloxytetrahydrofuran (chemical formula below) was obtained. As recrystallized from chloroform-isopropyl ether, colorless crystals, m.p. 157°–159° C., optical rotation $[\alpha]_D$ –142.8° (C=0.65, CHCl$_3$)

TABLE 14

$$\begin{array}{c}(CH_2)_2-O\\|\quad\quad|\\R-NH-CH-CH-OH\\(S)\quad\quad(RS)\end{array}$$

| Example No. | R | Melting point (°C.) | Recrystallization solvent | Optical rotation $[\alpha]_D$ (conc./solvent) |
|---|---|---|---|---|
| 93 | quinolyl—CO—(L)—Phe— | 183–185 | Ethyl acetate-methanol | +24.1° (c = 0.51, CHCl$_3$) |
| 94 | quinolyl—CO—(L)—Ile— | 78–83[1)] | | +62.9° (c = 0.60, CHCl$_3$) |
| 95 | 3-quinolyl—CO—(L)—Phe— | 185–187[2)] | Ethyl acetate-isopropyl ether | –38.1° (c = 0.34, DMSO) |
| 96 | 3-quinolyl—CO—(L)—Leu— | 117–119[3)] | Ethyl acetate | +64.6° (c = 0.37, DMSO) |
| 97 | Cbz—NH(CH$_2$)$_3$CO—(L)—Phe— | 154–157 | Chloroform-methanol-ether | –12.9° (c = 0.30, DMSO) |
| 98 | Cbz—NH(CH$_2$)$_3$CO—(L)—Leu— | 136–138 | Chloroform-ether | –33.5° (c = 0.31, DMSO) |

[1)]amorphous solid, ½ hydrate  [2)]¼ hydrate  [3)]¼ hydrate
Cbz: benzyloxycarbonyl, Leu: leucine, Phe: phenylalanine, Ile: isoleucine, DMSO: dimethyl sulfoxide

EXAMPLES 99–106

The compounds listed in Table 15 were synthesized in substantially the same manner as Example 54.

TABLE 15

$$\begin{array}{c}(CH_2)_2-O\\|\quad\quad|\\R-NH-CH-CH-OCOCH_3\\(S)\quad\quad(S)\end{array}$$

| Example No. | R | Melting point (°C.) | Recrystallization solvent | Optical rotation $[\alpha]_D$ (conc./solvent) |
|---|---|---|---|---|
| 99 | quinolyl—CO—(L)—Phe— | 175–176 | Ethyl acetate-hexane | –37.8° (c = 0.50, CHCl$_3$) |
| 100 | quinolyl—CO—(L)—Ile— | 161–164 | Ethyl acetate-hexane | –12.9° (c = 0.98, CHCl$_3$) |
| 101 | 3-quinolyl—CO—(L)—Phe— | 193–194[1)] | Ethyl acetate-methanol | –51.2° (c = 0.59, CHCl$_3$) |
| 102 | 3-quinolyl—CO—(L)—Leu— | 183–184[2)] | Chloroform-isopropyl ether | –53.8° (c = 0.59, CHCl$_3$) |
| 103 | Cbz—NH(CH$_2$)$_3$CO—(L)—Phe— | 183–184 | Ethyl acetate-methanol | –66.6° (c = 0.49, CHCl$_3$) |
| 104 | Cbz—NH(CH$_2$)$_3$CO—(L)—Leu— | 152–154 | Ethyl acetate-hexane | –79.2° (c = 0.53, CHCl$_3$) |
| 105 | (1,2,4-triazol-1-yl)—(CH$_2$)$_3$—CO—(L)—Phe— | 149–151 | Chloroform-isopropyl ether | –71.9° (c = 0.41, CHCl$_3$) |
| 106 | (C$_3$H$_7$)$_2$NCH$_2$—CO—(L)—Phe— | oil[3)] | | –74.5° (c = 0.48, CHCl$_3$) |

[1)]¼ hydrate  [2)]½ hydrate  [3)]NMR (δ ppm in CDCl$_3$): 0.84 (6H, t, J = 7.4 Hz), 1.30–1.45 (4H, m), 1.70–1.88 (1H, m), 2.01 (3H, s), 2.20–2.40 (5H, m), 3.00 (2H, s), 3.07 (2H, d, J = 7.6 Hz), 3.85–4.14 (4H, m), 4.20–4.61 (2H, m), 5.92 (1H, d, J = 4.6 Hz), 6.29 (1H, d, J = 8.4 Hz), 7.21–7.30 (5H, m), 7.86 (1H, d, J = 8 Hz).
Cbz: benzyloxycarbonyl, Leu: leucine, Phe: phenylalanine, Ile: isoleucine

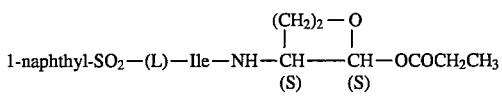

EXAMPLE 108

In substantially the same manner as Example 73, (3S)-3-[[N-benzyloxycarbonyl-(L)-phenylalanyl]amino]-2methoxytetrahydrofuran (chemical formula below) was obtained. As recrystallized from ethyl acetate-hexane, colorless crystals, m.p. 140°–142° C., optical rotation $[\alpha]_D$+17.1° (c=0.51, $CHCl_3$)

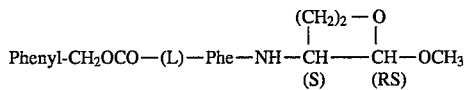

EXAMPLE 109

In substantially the same manner as Example 73, ethyl [(3S)-3-[[N-benzyloxycarbonyl-(L)-phenylalanyl]amino] tetrahydrofuran-2-yl]oxyacetate (chemical formula below) was obtained. As recrystallized from ether-isopropyl ether, colorless crystals, m.p. 103°–106° C., optical rotation $[\alpha]_D$ +14.9° (c=0.49, $CHCl_3$).

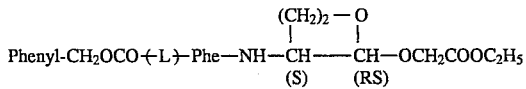

What is claimed is:

1. A compound of the general formula

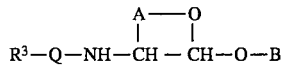

wherein Q represents one or two amino acid residues which may or may not be substituted; $R^3$ represents a carboxyl group which may or may not be esterified or an acyl group; A represents a C2–C4 alkylene group; B represents hydrogen, an alkyl group which may or may not be substituted or an acyl group; or a salt of the compound.

2. A compound of the general formula

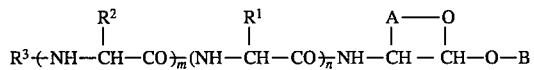

wherein $R^1$ and $R^2$ may be the same or different and each represents hydrogen or a hydrocarbon group which may or may not be substituted; $R^3$ represents a carboxyl group which may or may not be esterified or an acyl group; A represents C2–C4 alkylene group; B represents hydrogen, an alkyl group which may or may not be substituted or an acyl group; m represents 1 and n represents 1 or 0; or a salt of the compound.

3. The compound according to claim 1 or 2 wherein the alkyl group for B which may or may not be substituted represents a $C_{1-4}$ lower alkyl group which may or may not be substituted, or a salt of the compound.

4. The compound according to claim 1 or 2 wherein the acyl group for B represents an acyl group derived from a carboxylic acid which may or may not be substituted, or a salt of the compound.

5. The compound according to claim 2 wherein the hydrocarbon group for $R^1$ or $R^2$, which may or may not be substituted represents an aryl group which may or may not be substituted or an aliphatic hydrocarbon group which may or may not be substituted, or a salt of the compound.

6. The compound according to claim 5 wherein the aryl group for $R^1$ or $R^2$, which may or may not be substituted represents a $C_{6-14}$ aromatic hydrocarbon group of a monocyclic or a condensed polycyclic system, or a 5- or 6-membered heteroaromatic group, or a salt of the compound.

7. The compound according to claim 5 wherein the aliphatic hydrocarbon group for $R^1$ or $R^2$ represents (i) a saturated $C_{1-8}$ aliphatic hydrocarbon group, (ii) an unsaturated $C_{2-8}$ aliphatic hydrocarbon group (iii) a saturated $C_{3-7}$ alicyclic hydrocarbon group (iv) an unsaturated $C_{5-7}$ alicyclic hydrocarbon group or (v) a saturated $C_{1-8}$ aliphatic hydrocarbon group which is substituted by a alicyclic hydrocarbon group, or a salt of the compound.

8. The compound according to claim 2 wherein $R^1$ or $R^2$ represents a lower alkyl group, or a salt of the compound.

9. The compound according to claim 2 wherein $R^1$ or $R^2$ represents a arylalkyl group, or a salt of the compound.

10. The compound according to claim 1 or 2 wherein the acyl group for $R^3$ represents an acyl group derived from the group consisting of a carboxylic acid, a sulfonic acid, a sulfinic acid, a carbamic acid and a thiocarbamic acid, all of which may or may not be substituted, or a salt of the compound.

11. The compound according to claim 1 or 2 which is selected from the group consisting of (3S)-3-[[N-tert-butoxycarbonyl-(L)-phenylalanyl] amino]-2-hydroxytetrahydrofuran, (3S)-2-hydroxy-3-[[N-valproyl-(L)-valyl]amino] tetrahydrofuran, (3S)-2-hydroxy-3-[[N-(1-naphthylcarbamoyl)-(L)-leucyl]amino]tetrahydrofuran, (2S, 3S)-2-acetoxy-3-[[N-(1-naphthylcarbamoyl)-(L)-phenylalanyl]amino]tetrahydropyran, (3S)-2-hydroxy-3-[[N-(2-quinolylcarbonyl)-(L)-leucyl]amino]tetrahydrofuran, (2S,3S)-2-acetoxy-[[N-(2-quinolylcarbonyl)-(L)-leucyl] amino]tetrahydrofuran, (3S)-3-[[N-benzyloxycarbonyl-(L)-tyrosl]amino]-2-methoxytetrahydrofuran and (2S,3S)-3-[ [N-(1-naphthalensulfonyl)-(L)-isoleucyl]amino]-2-propionyloxytetrahydrofuran, or salt of the compound.

12. A compound selected from (3S)-3-[[N-dibenzylacetyl]amino]-2-hydroxytetrahydrofuran and (3S)-3-[[N-7, 7-diphenyl-6-heptenyoyl]amino]-2-hydroxytetrahydrofuran, or a salt of the compound.

13. A pharmaceutical composition comprising an effective amount of the compound of claim 1 or claim 2 and a pharmaceutically acceptable carrier.

14. A cathepsin L inhibitory composition comprising a compound of the general formula.

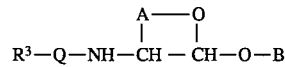

wherein Q represents one or two amino acid residues which may or may not be substituted; $R^3$ represents a carboxyl group which may or may not be esterified or an acyl group; A represents a C2–C4 alkylene group; B represents hydrogen, an alkyl group which may or may not be substituted or an acyl group; or a medicinally acceptable salt of the compound.

15. A cathepsin L inhibitory composition comprising a compound of the general formula

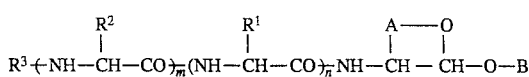

wherein $R^1$ and $R^2$ may be the same or different and each represents hydrogen or a hydrocarbon residue which may or may not be substituted; $R^3$ represents a carboxyl group which may or may not be esterified or an acyl group; A represents C2–C4 alkylene group; B represents hydrogen or an alkyl group which may or may not be substituted or an acyl group; m represents 1 and n represents 1 or 0, or a medicinally acceptable salt of the compound.

16. A bone resorption inhibitory composition comprising a compound of the general formula

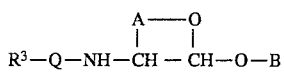

wherein Q represents one or two amino acid residues which may or may not be substituted; $R^3$ represents a carboxyl group which may or may not be esterified or an acyl group; A represents an alkylene group; B represents hydrogen or an alkyl group which may or may not be substituted or an acyl group; or a medicinally acceptable salt of the compound.

17. A bone resorption inhibitory composition comprising a compound of the general formula

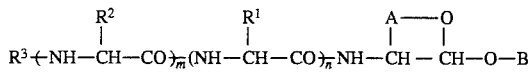

wherein $R^1$ and $R^2$ may be the same or different and each represents hydrogen or a hydrocarbon residue which may or may not be substituted; $R^3$ represents a carboxyl group which may or may not be esterified or an acyl group; A represents C2–C4 alkylene group; B represents hydrogen or an alkyl group which may or may not be substituted or an acyl group; m represents 1 and n represents 1 or 0, or a medicinally acceptable salt of the compound.

18. A bone resorption inhibitory composition according to claim 16 or 17 for the prophylaxis or therapy of osteoporosis.

19. A cathepsin L inhibitory composition according to claim 14 or 20 for the prophylaxis or therapy of osteoporosis.

20. A method for prophylaxis or treatment of a mammal suffering from osteoporosis which comprises administering to said mammal an effective amount of a compound of the formula

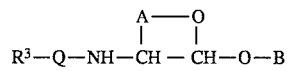

wherein Q represents one or two amino acid residues which may or may not be substituted; $R^3$ represents a carboxyl group which may or may not be esterified or an acyl group; A represents a C2–C4 alkylene group; B represents hydrogen, an alkyl group which may or may not be substituted or an acyl group; or a medicinally acceptable salt of the compound.

21. A method for prophylaxis or treatment of a mammal suffering from osteoporosis which comprises administering to said mammal an effective amount of a compound of the formula

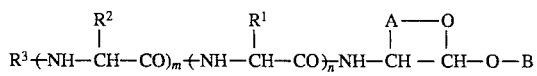

wherein $R^1$ and $R^2$ may be the same or different and each represents hydrogen or a hydrocarbon residue which may or may not be substituted; $R^3$ represents a carboxyl group which may or may not be esterified or an acyl group; A represents a C2–C4 alkylene group; B represents hydrogen or an alkyl group which may or may not be substituted or an acyl group; m and n each represents 0 or 1, or a medicinally acceptable salt of the compound.

22. The method of claim 21 wherein m represents 1.

* * * * *